(12) United States Patent
Fronticelli et al.

(10) Patent No.: US 7,329,641 B2
(45) Date of Patent: Feb. 12, 2008

(54) BLOOD SUBSTITUTES

(75) Inventors: Clara Fronticelli, Timonium, MD (US); William S. Brinigar, Yardley, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 176 days.

(21) Appl. No.: 10/979,483

(22) Filed: Nov. 1, 2004

(65) Prior Publication Data

US 2005/0227912 A1 Oct. 13, 2005

Related U.S. Application Data

(60) Provisional application No. 60/515,759, filed on Oct. 30, 2003.

(51) Int. Cl.
*C07K 14/805* (2006.01)
(52) U.S. Cl. .......................... 514/6; 530/385
(58) Field of Classification Search ................ 435/585; 514/6; 530/385
See application file for complete search history.

(56) References Cited

U.S. PATENT DOCUMENTS

| | | | |
|---|---|---|---|
| 4,584,130 A | 4/1986 | Bucci et al. | 260/112 |
| 5,028,588 A | 7/1991 | Hoffman et al. | 514/6 |
| 5,239,061 A | 8/1993 | Fronticelli et al. | 530/385 |
| 5,290,919 A | 3/1994 | Bucci et al. | 530/385 |
| 5,387,672 A | 2/1995 | Bucci et al. | 530/385 |
| 5,661,124 A | 8/1997 | Hoffman et al. | 514/6 |
| 5,753,465 A | 5/1998 | Ho et al. | 435/69.6 |
| 5,888,766 A | 3/1999 | Ishizuka et al. | |
| 6,124,114 A | 9/2000 | Hoffman et al. | 534/69.1 |
| 6,780,892 B1 | 8/2004 | Fronticelli | 516/6 |

FOREIGN PATENT DOCUMENTS

WO  WO 00/18802  4/2000

OTHER PUBLICATIONS

Springer, Barry A., Sligar, Stephen G., "High-level expression of sperm whale myoglobin in *Escherichia coli*," Dec. 1987, vol. 84, pp. 8961-8965, Proc. Natl. Acad. Sci. USA, Biochemistry.

Carver, Theodore E., Brantley, Jr., Robert E., Singleton, Arduini, Robert M., Quillin, Michael L., Phillips, Jr., George N., Oson, John S., "A Novel Site-Directed Mutant of Myoglobin with an Unusually High $O_2$ Affinity and Low Autooxidation Rate," vol. 267, No. 2, Issue of Jul. 15, pp. 14443-14450, 1992, The Journal of Biological Chemistry (Advertisement).

Springer, Barry A., Sligar, Stephen g., Olson, John S., Phillips, Jr., George N., "Mechanisms of Ligand Recognition in Myoglobin," Chem. Rev. 1994, vol. 94, pp. 699-714.

La Mar, Gerd N., Dalichow, Frank, Zhao, Xuefeng, Dou, Yi, Ikea-Saito, Masao, Chiu, Mark L., Sligar, Stephen G., "IH NMR Investigation of Distal Mutant Deoxy Myoglobins," Nov. 25, 1994, vol. 269, No. 47, pp. 29629-29635, The Journal of Biological Chemistry.

Dou, Yi, Maillett, David H., Eich, Raymund F., Olson, John S., "Myoglobin as a model system for designing heme protein based blood substitutes," 2002, pp. 127-148, Biophysical Chemistry.

Liong, Elaine C., Dou, Yi, Scott, Emily E., Olson, John S., Phillips, Jr., George N., "Waterproofing the Heme Pocket, Role of Proximal Amino Acid Side Chains in Preventing Hemin Loss From Myoglobin," Issue of Mar. 23, 2001, vol. 276, No. 12, pp. 9093-9100, The Journal of Biological Chemistry.

Bobofchak, Kevin M., Mito, Toshiaki, Texel, Sarah J., Bellelli, Andrea, Nemoto, Masaaki, Traystman, Richard J., Koehler, Raymond C., Brinigar, William S., Fronticelli, Clara, "A recombinant polymeric hemoglobin with conformational, functional, and physiological characteristics of an in vivo $O_2$ transporter," 2003, *Am J Physiol Heart Circ Physiol* 285, pp. H549-H561, Apr. 10, 2003, Kcc Apr. 23, 2007.

Fronticelli, C, Brinigar, WS, Olson, JS, Bucci E, Gryczynski, Z, O'Donnell Kowalczyk, J., "Recmbinant human hemoglobin: modification of the polarity of beta-heme pocket by a valine67(E11)→threonine mutation," Biochemistry. Feb. 9, 1993;32(5):1235-42. PMID: 8448134 [Pubmed—indexed for MEDLINE].

Pechik I, Ji X, Fidelis K, Karavitis M, Moult J, Brinigar WS, Fronticelli C, Gilliland GL, "Crystallographic, molecular modeling, and biophysical characterization of the valine beta 67 (E11)→threonine variant hemoglobin," Biochemistry. Feb. 13, 1996;35(6): 1935-45, PMID: 8639677 (PubMed—indexed for MEDLINE].

Fronticelli C, Arosio D, Bobofchak KM, Vasquez GB, "Molecular engineering of a polymer of tetrameric hemoglobins," Proteins. Aug. 15, 2001;44(3):212-22, PMID: 11455594 [PubMed—indexed for MEDLINE].

Karavitis, Michael, Fronticelli, Clara, Brinigar, William S., Vasquez, Gregory B., Militello, Valeria, Leone, Maurizio, Cupane, Antonio, "Properties of Human Hemoglobins with Increased Polarity in the α- or β-Heme Pocket," The Journal of Biological Chemistry, vol. 273, No. 37, Issue of Sep. 11, pp. 23740-23749, 1998.

Kao, Yung-Hsiang, Fitch, Carolyn A., Bhattacharya, Shibani, Sarkisian, Christopher J., Lecomte, Juliette T.J., Garcia-Moreno E., Bertrand, Dr., "Salt Effects on Ionization Equilibria of Histidines in Myoglobin," Biophysical Journal, vol. 79, Sep. 2000, pp. 1637-1654.

Kroll, J. et al.; *Chemical reactions of Benzyl Isothiocyanate with Myoglobin*; 1996 J. Sci. Food Aric., vol. 72, pp. 376-384.

*Primary Examiner*—Karen Cochrane Carlson
(74) *Attorney, Agent, or Firm*—William J. McNichol, Jr.

(57) ABSTRACT

The functional characteristics of heme proteins can be modified to produce hemoglobins that can be used as blood substitutes in different therapeutic applications. Stable polymers of tetrameric hemoglobin, and of myoglobin molecules, are provided for use in the blood substitutes.

26 Claims, 9 Drawing Sheets

BLOOD SUBSTITUTES

CROSS REFERENCE TO RELATED APPLICATION

This application claims the benefit of co-pending U.S. provisional patent application Ser. No. 60/515,759, filed on Oct. 30, 2003, the entire disclosure of which is herein incorporated by reference.

REFERENCE TO GOVERNMENT GRANT

The present invention was made at least partly with government funds under grant nos. HL 48517 and NS 38684 from the National Institute of Health. The U.S. government may have certain rights in the invention.

FIELD OF INVENTION

This invention relates to novel modified heme protein compositions useful as blood substitutes, and to methods of preparing the blood substitutes and the modified heme proteins.

BACKGROUND OF THE INVENTION

In medicine, the need for transfusional fluids is continually increasing. The use of stroma-free hemoglobin (Hb) solutions as a red cell replacement has been considered. Solutions of stroma-free Hb contain tetrameric (MW 64 kDa) and dimeric (MW 32 kDa) Hb molecules at equilibrium. Due to the rapid filtration of the dimers through the kidneys, the retention time of infused Hb solutions is short. In addition, Hb molecules extravasate through the endothelium, scavenging the NO from the interstitial fluid. The latter is believed to be the main reason for the increase in mean arterial pressure observed upon administration of a stroma-free Hb solution.

Chemical modifications have been used to transform mammalian Hbs into efficient blood substitutes, but the introduction of such chemical modifications can result in toxicity and/or an immunogenic response. For example, much work has been devoted to the preparation of Hb solutions with oxygen affinities similar to that of whole blood. Recent studies, however, indicate that Hb with high oxygen affinity can efficiently deliver $O_2$ to the tissues. Thus, the question of optimal oxygen affinity for blood substitutes has not been resolved.

Adult Hb is a tetrameric protein comprised of two structurally similar subunits, $\alpha$ and $\beta$, assembled through two different interfaces. Each subunit contains eight $\alpha$-helices (labeled A-H) that form a pocket containing the heme. The heme pocket of each subunit is lined by hydrophobic residues, except for the proximal (F8) and distal (E7) histidines, which are critical to the functional properties of Hb. The functional properties of the heme pocket are also greatly sensitive to the polar character of the amino acid side chains lining the pocket.

As previously mentioned, problems related to the use of Hb solutions for transfusion include the rapid loss of Hb through the kidneys and vasoconstriction with an increase in arterial blood pressure, which is thought to be due to scavenging of NO released from the endothelium. Moreover, at the physiological colloid-osmotic pressure of human plasma, only a limited amount of Hb may safely be infused, and thus the oxygen-carrying capacity of blood cannot be fully restored. In an effort to prevent these effects, tetramers of Hb molecules that resist dissociation into dimers in serum have been produced by using bifunctional reagents to effect intramolecular crosslinking. In the absence of further intermolecular crosslinking, stabilized tetrameric Hbs still extravasated across the endothelium and failed clinical tests. See, e.g., Saxena et al., 1999, *Stroke*. 30: 993-996 and Sloan et al., 1999, *JAMA* 282: 1857-1864.

Myoglobin (Mb) is a 17.5 kilodalton monomeric heme protein found mainly in muscle tissue, where it serves as an intracellular storage site for oxygen. During periods of oxygen deprivation, oxymyoglobin releases its bound oxygen which is then used for metabolic purposes.

The tertiary structure of Mb is that of a typical water soluble globular protein, and contains approximately 75% $\alpha$-helical secondary structure. A Mb polypeptide is comprised of eight separate right handed $\alpha$-helices, designated A through H, that are connected by short non-helical regions. Amino acid R-groups oriented towards the interior of the molecule are predominantly hydrophobic in character, and those on the surface of the molecule are generally hydrophilic, thus making the molecule relatively water soluble. Each Mb molecule contains one heme prosthetic group inserted into a hydrophobic cleft in the protein. To date, an adequate blood substitute which utilizes Mb is not available.

The curve of oxygen binding to Hb is sigmoidal, which is typical of allosteric proteins in which the substrate, in this case oxygen, is a positive homotropic effector. When oxygen binds to the first subunit of deoxyhemoglobin, the first oxygen molecule increases the affinity of the remaining subunits for additional oxygen molecules. As additional oxygen is bound to the other Hb subunits, oxygen binding is incrementally strengthened, so that Hb is fully oxygen-saturated at the oxygen tension of lung alveoli. Likewise, oxygen is incrementally unloaded and the affinity of Hb for oxygen is reduced as oxyhemoglobin circulates to deoxygenated tissue.

In contrast, the oxygen binding curve for Mb is hyperbolic in character, indicating the absence of allosteric interactions in this process. Mb therefore has a higher oxygen affinity and lower cooperativity than Hb. A large array of Mb heme pocket mutants have been constructed and investigated (Springer et al., *Chem Rev* 1994; 94: 699-714), and information is thus available on the molecular control of the conformational and functional properties of Mb. While these studies are certainly useful in the design of Hb-based oxygen carriers (Dou et al., *Biophys Chem* 2002; 98: 127-148), heme pocket differences exist between Mb and Hb. The effect of a particular mutation in Mb is therefore not necessarily predictive of the effect the analogous mutation would have in Hb.

Abbreviations

Hb—hemoglobin
HbA—human Hb
PolyHb—polymerized Hb
Mb—Myoglobin
PolyMb—polymerized Mb
ZL-Hb$_{Bv}$—chemically cross-linked bovine Hb
$\beta L^{28}$(B10)N—recombinant HbA, in which $\beta Lys^{28}$(B10) was replaced by Asn
$\beta V^{67}$(E11)T—recombinant HbA, in which $\beta Va^{67}$(E11) was replaced by Thr
$\alpha V^{63}$(E11)T—recombinant HbA, in which $\alpha Val^{63}$(E11) was replaced by Thr
PB4—recombinant HbA with mutations $\beta(^{V1M+H2deleted+T4I+P5A})$ PB5—recombinant HbA with mutations $\beta(^{V1M+H2deleted+T4I+P5A+A76K})$ Hb Prisca—recombinant HbA with mutations $\beta(^{S9C+C93A+C112G})$ Hb Minotaur ($\alpha_H\beta_{Bv}$)—Hybrid Hb containing α-human and β-bovine chains Hb Polytaur—polymerized Hb Minotaur with mutations ($\alpha_H^{C104S}\beta_{Bv}^{A9C+C93A}$)

Hb (Polytaur)$_n$—polymerized Hb Minotaur with mutations ($\alpha_H\beta_{Bv}^{A9C}$)

SUMMARY OF THE INVENTION

Figure 1:
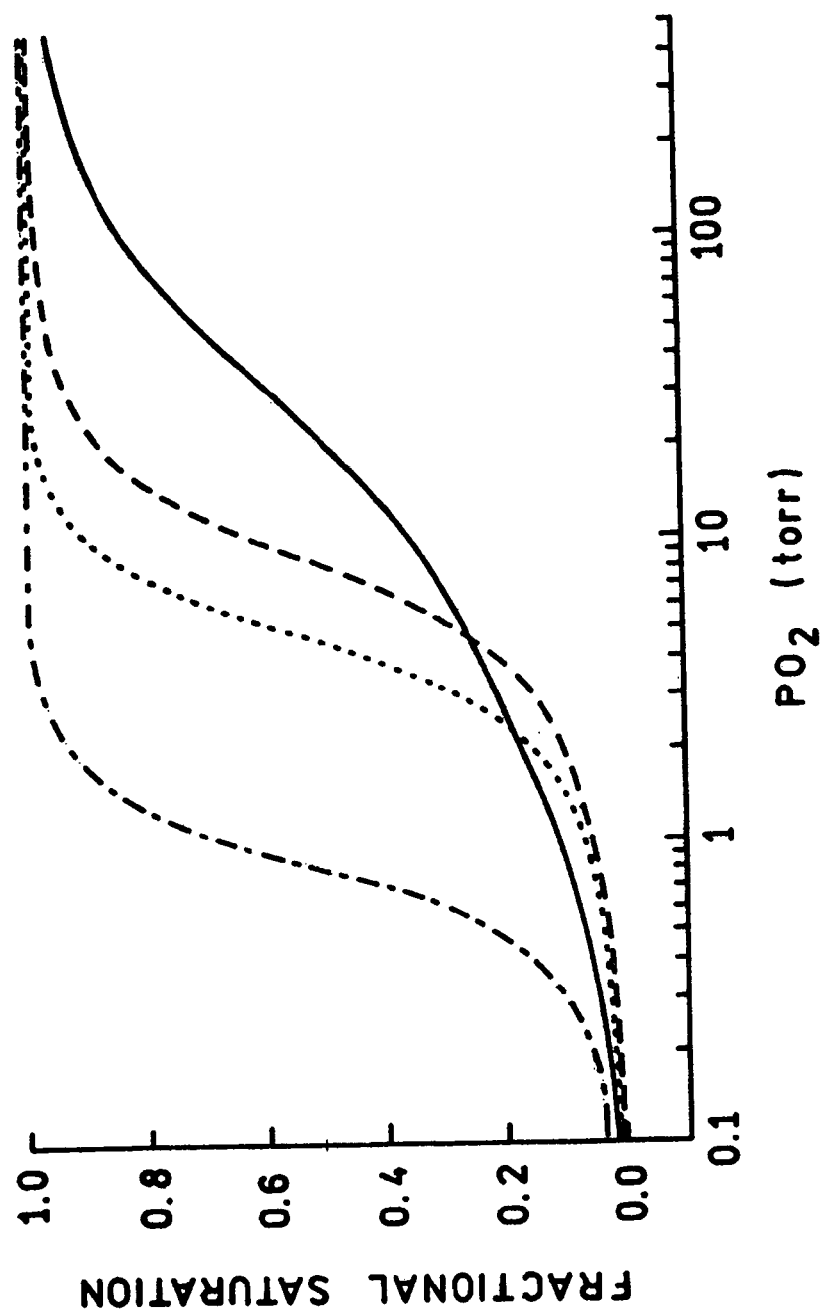
FIG. 1 is a graph showing the oxygen affinity of $\beta L^{28}$ (B10)N (-.-.); HbA ( . . . ); $\beta V^{67}$ (E11)T (- -); $\alpha V^{63}$ (E11)T (-). Measurements were carried out using the Gill cell with an AVIV 14DS spectrophotometer. Protein concentration was 1.5 mM in heme. Buffer (pH 7.4, 50 mM Hepes+100 mM NaCl): Temperature 25° C.

The functional characteristics of heme proteins have been modified to produce Hbs that can be used as resuscitating fluids (i.e., blood substitutes) in different therapeutic applications. For example, modification at the heme pocket can produce Hbs with a range of oxygen affinities. Stable polymers of tetrameric Hb molecules of different sizes and with different oxygen affinities have therefore been obtained. Modifications on the protein surface produced a human Hb with decreased oxygen affinity, regulated by the concentration of chlorides in the plasma. Blood substitutes comprising modified Mb can also be produced. For example, modified Mb can be induced to form stable polymers. The polymerization of such modified Mb does not alter the functional characteristics of the component monomeric Mb. Polymeric Mbs can therefore be constructed with additional mutations to engineer functional characteristics tailored to different clinical applications.

The invention thus provides an isolated Hb comprising a first and a second polypeptide having the amino acid sequence of the normal human Hb alpha chain, and a third and fourth polypeptide having the sequence of normal bovine Hb beta chain. At least one polypeptide of the isolated Hb comprises at least one mutation which introduces a polymerization site. In one embodiment, the at least one mutation comprises the substitution of the alanine at position 9 for cysteine on at least one of the normal bovine Hb beta chains. In bovine Hb beta chains, the histidine corresponding to position beta2 in HbA is missing. For the purposes of the present invention, a number has been assigned to this position in bovine Hb for consistency in numbering the amino acid residues. In another embodiment, the at least one mutation comprises a mutation of residue 104 in the normal human Hb alpha chain from cysteine to serine, and a mutation of residue 9 from alanine to cysteine and a mutation of residue 93 from cysteine to alanine in the normal bovine Hb beta chain.

The invention also provides an isolated hemoglobin molecule comprising at least one human hemoglobin subunit polypeptide and at least one non-human mammalian hemoglobin subunit polypeptide.

The invention further provides a polymer comprising an isolated modified Hb of the invention.

The invention further provides a polypeptide comprising a subunit of the modified Hb of the invention, and a nucleic acid comprising a nucleotide sequence encoding the polypeptide subunit.

The invention further provides a method of producing the isolated modified Hb of the invention, comprising modifying at least two polypeptide subunits of the Hb with at least one mutation that introduces a polymerization site.

The invention also provides a polymer comprising a plurality of modified Mb monomers, in which the Mb monomers comprise at least one modification which introduces a polymerization site. The modification which introduces a polymerization site in the Mb monomers can comprise a chemical modification or a mutation in the Mb monomer.

The invention also provides a Mb monomer modified to include a polymerization site, and a nucleic acid comprising a nucleotide sequence encoding the Mb monomer.

The invention further provides a method of producing the Mb monomer of the invention, comprising modifying at least one Mb monomer to introduce a polymerization site in the monomer.

The invention still further provides a method of producing an isolated Mb polymer of the invention, comprising modifying at least one Mb monomer to introduce a polymerization site, and subjecting the modified Mb monomer to conditions which cause the monomers to polymerize.

The invention still further provides a blood substitute comprising a modified heme protein of the invention.

The invention still further provides a method of supplementing the oxygen-carrying capacity of a subject's blood, comprising administering to the patient an effective amount of the blood substitute comprising an isolated modified heme protein of the invention, or a polymer thereof. Where the isolated modified heme protein of the invention is a Hb, the Hb comprises a first and a second polypeptide having the amino acid sequence of the normal human Hb alpha chain, and a third and fourth polypeptide having the sequence of normal bovine Hb beta chain, and wherein at least one polypeptide comprises at least one mutation which introduces a polymerization site. Where the isolated modified heme protein of the invention is a Mb, the Mb comprises at least polymerization site.

DETAILED DESCRIPTION OF THE INVENTION

Blood substitutes can be constructed which comprise modified oxygen-binding heme proteins, such as modified hemoglobin (Hb) or modified myoglobin (Mb) or polymers thereof.

Human adult Hb, designated Hb A, comprises two alpha and two beta polypeptide subunits. The alpha subunit consists of 141 amino acids. The iron atom of the heme (ferroprotoporphyrin IX) group is bound covalently to the imidazole of His87 (the "proximal histidine") of the alpha subunit. The beta subunit is 146 residues long, and the heme group is bound to this subunit at His 92.

The primary amino acid structure of the human adult Hb (HbA) alpha and beta subunits, and the nucleic acid sequences which encode them, are known in the art (see Wilson et al., *J. Biol. Chem.*, 1980, 255(7), 2807-2815, the entire disclosure of which is herein incorporated by reference. The HbA subunit amino acid sequences are presented herein as SEQ ID NO: 1 (alpha subunit) and SEQ ID NO: 2 (beta subunit). The nucleotide sequences encoding the HbA alpha and beta subunits are presented herein as SEQ ID NO: 3 and SEQ ID NO: 4, respectively. Likewise, the bovine Hb ($Hb_{Bv}$) beta subunit amino acid sequence is known in the art (see, e.g., Schimenti et al., *Nucleic Acids Res.*, 1984, 12(3), 1641-1655 and Bobofchak et al., *Am J Physiol Heart Circ Physiol* 2003; 285: H549-61, the entire disclosures of which are herein incorporated by reference and are provided herein as SEQ ID NO: 5. The nucleic acid sequence encoding the $Hb_{Bv}$ beta subunit represented by SEQ ID NO: 5 is presented herein as SEQ ID NO: 6.

Various mutations have been introduced into the alpha and beta subunits of HbA which have altered the oxygen affinity of the modified Hbs. Such modified HbA have been previously described, and their functional characteristics are presented in Table 2 below. However, it was not always possible to obtain sufficient amounts of recombinant HbA. Therefore, a tetrameric hybrid Hb comprising two human alpha subunits and two bovine subunits (called "Hb Minotaur") was constructed; see Bobofchak et al., supra. Hb Minotaur can be expressed in *Escherichia coli* at considerably higher levels than all-human Hbs, and has the same oxygen affinity as HbA. Hb Minotaur can be used as the starting point for construction of modified Hb of the invention, in which at least one polymerization site is introduced into at least one Hb subunit. An isolated molecule comprising, or consisting essentially of, Hb Minotaur is therefore considered to be part of the present invention.

The invention also provides an isolated hemoglobin molecule comprising, or consisting essentially of, at least one human hemoglobin subunit polypeptide and at least one non-human mammalian hemoglobin subunit polypeptide. Such isolated hemoglobin molecules are referred to herein as "hybrid hemoglobin molecules." Preferably, a hybrid hemoglobin molecule comprises two of the same human hemoglobin subunit polypeptides (e.g., two human alpha or beta subunit polypeptides) and two of the same non-human mammalian hemoglobin subunit polypeptides (e.g., two non-human mammalian alpha or beta subunit polypeptides). However, a hybrid hemoglobin molecule can comprise at two different human or non-human hemoglobin subunit polypeptides; for example, a hybrid hemoglobin can comprise one human and alpha and one human beta subunit polypeptide, or one non-human mammalian alpha and one non-human mammalian beta subunit polypeptide. Preferably, the hybrid hemoglobin comprises at least two of the same hemoglobin subunit polypeptides from a given human or non-human mammalian species.

The primary amino acid sequences (and the corresponding nucleic acid sequences which encode them) for mammalian hemoglobin subunit polypeptides are known in the art, and can be readily obtained by one skilled in the art. In addition to the bovine hemoglobin beta subunit polypeptide sequences described above, representative non-human mammalian hemoglobin subunit polypeptides are given in SEQ ID NOS: 18 to 35, as indicated in Table 1.

TABLE 1

| Organism | Hb subunit | Sequence Type | SEQ ID NO. |
|---|---|---|---|
| *Rattus norvegicus* | alpha | protein | 18 |
| *Rattus norvegicus* | alpha | nucleic acid | 19 |
| *Rattus norvegicus* | beta | protein | 20 |
| *Rattus norvegicus* | beta | nucleic acid | 21 |
| *Mus musculus* | alpha | protein | 22 |
| *Mus musculus* | alpha | nucleic acid | 23 |
| *Mus musculus* | beta (major) | protein | 24 |
| *Mus musculus* | beta (major) | nucleic acid | 25 |
| *Mus musculus* | beta (minor) | protein | 26 |
| *Mus musculus* | beta (minor) | nucleic acid | 27 |
| *Bos taurus* | alpha (allele Y) | protein | 28 |
| *Bos taurus* | alpha (allele Y) | nucleic acid | 29 |
| *Bos taurus* | alpha (allele S) | protein | 30 |
| *Bos taurus* | alpha (allele S) | nucleic acid | 31 |
| *Bos taurus* | alpha (allele N) | protein | 32 |
| *Bos taurus* | alpha (allele N) | nucleic acid | 33 |
| *Sus scrofa* | alpha | protein | 34 |
| *Sus scrofa* | beta | nucleic acid | 35 |

As used herein, "isolated" refers to a molecule which is wholly or partially synthetic, or which is altered or removed from the natural state through human intervention. For example, a heme protein, such as a Hb or Mb (or subunit thereof) which is partially or completely separated from the coexisting materials of its natural state is "isolated." An isolated molecule of the invention can exist in substantially purified form, or can exist in a non-native environment such as, for example, a cell in which the molecule is produced or introduced, or a structure (such as the vasculature) into which the molecule has been delivered.

As used herein, a "polymerization site" on a heme protein polypeptide, such as a Hb subunit or Mb monomer, means any residue or region of the subunit polypeptide which has, or can be induced to have, the ability to form an intermolecular bond with another subunit. For example, a polymerization site can comprise a modification to an amino acid residue which provides that residue with a chemical group which can react with at least one amino acid residue (or chemical group thereon) on another subunit. Preferred polymerization sites comprise a naturally-occurring or non naturally-occurring cysteine. As used herein, a polymerization site can be "introduced" into a heme protein subunit by chemical techniques, or by mutating the amino acid sequence of the subunit to substitute one amino acid residue (e.g., a cysteine) for another. Techniques for mutating the amino acid sequence of a heme protein subunit are discussed in more detail below.

Isolated Hb subunits of the invention can therefore be produced by introducing a polymerization site into the molecule. These modified Hb subunits can then be assembled into functional Hb α2β2 tetramers, which in turn can be polymerized by subjecting the Hb α2β2 tetramers comprising the modified subunits to conditions which activate the polymerization sites. A suitable technique for activating polymerization sites is described in the Examples below.

In one embodiment, the amino acid sequence of at least one Hb subunit (e.g., at least one alpha or at least one beta subunit, preferably both alpha and both beta subunits) was mutated by substituting at least one amino acid residue located on the surface of the folded subunit polypeptide with a cysteine. Optionally, one or more naturally-occurring cysteines in a Hb subunit (if any) are substituted with amino acid residues which do not form intermolecular bonds.

For example, subunits of Hb Minotaur were modified to introduce polymerization sites by substituting a cysteine for alanine at position β9, and by substituting certain naturally occurring cysteines with amino acid residues that do not form intermolecular bonds. Preferably, the alpha subunit of Hb Minotaur is modified by substituting a serine for the cysteine at position α104, and beta subunit is modified by substituting a alanine for the cysteine at β93. The two modified subunits are then combined to form the isolated mutant Hb $\alpha_H^{C104S}\beta_{Bv}^{A9C+C93A}$, which is designated "Hb Polytaur" after polymerization. The biochemical characterization of Hb Polytaur is given in Table 2.

As can be seen from Table 2, intermolecular polymerization through S—S disulfide bonds at position β9 does not modify the oxygen affinity of Hb Polytaur, which remained similar to that of HbA (about 17.0 torr at 37° C.). However, the affinity of Hb Polytaur for heme was increased upon polymerization. Measurements of autoxidation rates under in vivo conditions (e.g., in whole blood) indicated the protective effect of blood components toward heme oxidation in Hb Polytaur. As can be seen from Table 2, the half-time of autoxidation of Hb Polytaur heme in blood is 46 h, which is about 15-fold longer than Hb Polytaur heme oxidation under in vitro conditions. This value indicates that within the approximately 20 h retention time in circulation measured in humans with other polymerized Hbs, only 25% of infused Hb Polytaur would be oxidized, while the remaining 75% would remain reduced and functionally active as an oxygen carrier.

In another embodiment, a modified Hb of the invention is produced by introducing a polymerization site in the beta subunits of Hb Minotaur by substituting a cysteine for the alanine at position β9. In this embodiment, there is no substitution of the naturally-occurring cysteines present at α104 and β93. The isolated Hb formed with the modified beta subunits ($\alpha_H\beta_{Bv}^{A9C}$) is called Hb (Polytaur)$_n$. Hb (Polytaur)$_n$ polymerizes more rapidly than Hb Polytaur.

Figure 4:
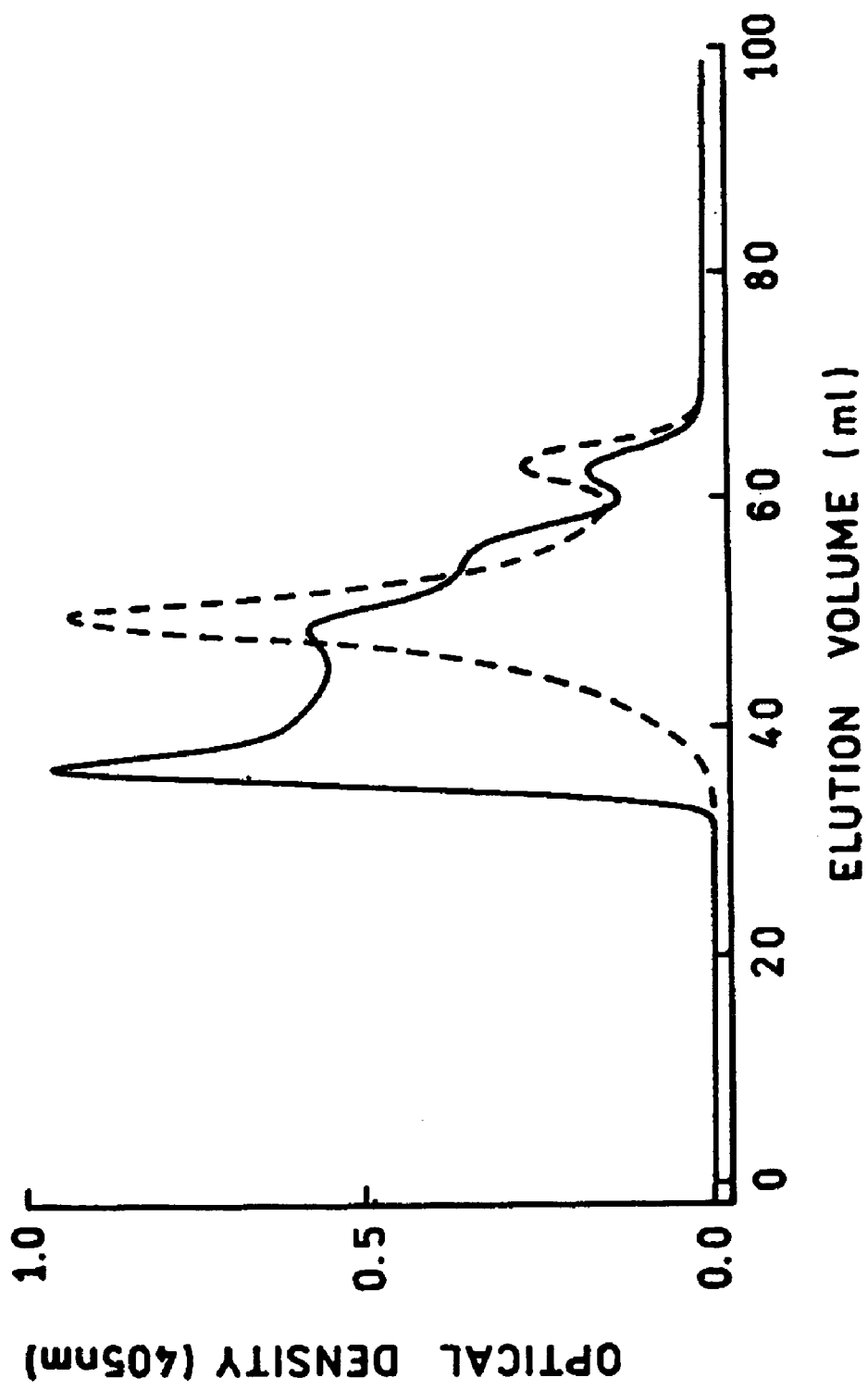
FIG. 4 is a graph showing the size exclusion chromatography of Hb Polytaur (--) and Hb (Polytaur)$_n$ (-). Hb Polytaur was eluted as a homogeneous peak as for the polymerization of ~7 tetrameric Hb molecules (MW=500 kDa). The elution pattern of Hb (Polytaur)$_n$ was heterogeneous with a large fraction eluted with the void volume of the column (35 ml). (MW=>1,000 kDa). Measurements were carried out at 4° C., on a fractoget EMD BioSec column. Buffer: 20 mM phosphate with 300 mM NaCl, pH 7.2.

Hb (Polytaur)$_n$ is a heterogeneous polymer with a molecular weight of about 1000 kilodaltons (kDa) or higher, as measured by size exclusion chromatography as shown in FIG. 4, where the elution patterns of Hb Polytaur and Hb (Polytaur)$_n$ are compared. Oxygen-binding measurements indicated that Hb (Polytaur)$_n$ had oxygen-binding characteristics similar to Mb; i.e., high oxygen affinity (P50=about 2.0 torr) and loss of cooperativity (n=1). Without wishing to be bound to any theory, it is believed that Hb (Polytaur)$_n$ has similar stability and heme affinity as that measured for Hb Polytaur.

As shown in the Examples below, vasoactivity was not observed following infusion of polymerized isolated Hb of the invention, from which any residual unpolymerized Hb molecules had been removed.

The biochemical characteristics of the polymerized isolated Hb of the invention can be compared to the biochemical characteristics of a known polymerized Hb (Hb Prisca), with normal HbA, and with various non-polymerized Hb molecules with modifications on surface or heme-pocket amino acids. These comparative biochemical characteristics are shown in Table 2.

TABLE 2

| | | | | NO release | Autoxidation $T_{1/2}$, h | | Heme transfer $T_{1/2}$, h | | Brain Infarct Reduction |
|---|---|---|---|---|---|---|---|---|---|
| | Mutations | $P_{50}$ (torr) | $n_{max}$ | $T_{1/2}$, h | In vitro | In blood | α-chains | β-chains | |
| Heme pocket | HbA | 6.5* | 2.9 | 260.0 | 36.0 (1.0)$^v$ | | 1.38 | 0.06 | |
| | | | | α-chains β-chains | α-chains β-chains | | | | |
| | β$V^{63}$(E11)T | 12.0* | 2.2 | 340    30 | 29.0 (0.5)  0.06 (0.5)$^v$ | — | 1.15 | 0.35 | |
| | α$V^{58}$(E11)T | 25.0* | <~1.1 | 15      380 | 0.03 (0.5)  29.0 (0.5)$^v$ | — | — | — | |
| | β$L^{28}$(B10)N | 0.64* | 1.8 | — | — | — | — | — | |
| Protein surface | HbA | 1.6$^\&$ | 2.8 | | 33.0 (1.0)$^v$ | | 4.6 | 0.4 | |
| | PB4 [β$^{V1M+H2Δ+T4I+P5A}$] | 4.0$^\&$ | 2.1 | | 10.0 (0.4), 138(0.6)$^v$ | | 4.2 | 0.2 | |
| | PB5 [β$^{V1M+H2Δ+T4I+P5A+A76K}$] | 12.0* | 2.4 | | 6.9 (0.3), 115 (0.7)$^v$ | | 2.3 | 0.1 | |
| Polymerization HbA α$_H$β$_H$ | HbA | 17.0° | 2.8 | | 63.0$^Λ$ | | | | |
| | HbPrisca [α$_H$β$_H^{(S9C+C93A+C112G)}$] | 17.0° | 2.3 | | 54.0$^Λ$ | | | | |
| Polymerization HbA α$_H$β$_{Bv}$ | HbA | 18.0° | 2.4 | | 33$^v$ | 160 | 3.4 | 0.32 | |
| | HbPolytaur [α$_H^{(C104S)}$β$_{Bv}^{(S9C+C93A)}$] | 16.0° | 1.7 | | 0.7 (0.25), 4.0 (0.75)$^v$ | 46 | 0.7 (30%), 5.5 (30%), | | 20% |

TABLE 2-continued

| | | | | NO release | Autoxidation $T_{1/2}$ h | | Heme transfer $T_{1/2}$ h | | Brain |
| | Mutations | $P_{50}$ (torr) | $n_{max}$ | $T_{1/2}$, h | In vitro | In blood | α-chains | β-chains | Infarct Reduction |
|---|---|---|---|---|---|---|---|---|---|
| Polymerization | Hb(Polytaur)$_n$ [α$_H$β$_{Bv}$$^{S9C}$] | ~2-3° | 1.0 | | | | 0.0 (40%) | | 40% |
| Myoglobin | Mb | 1.1 | 1.0 | | | | | | |
| | PolyMb [N8C + K50C + K76C] | 1.1 | 1.0 | | | | | | |

Regarding Table 2, due to differences in experimental conditions, comparisons can only be made within each study. *Gill cell[33] (pH 7.4, 25° C. 50 mM Hepes+100 mM NaCl); &Gill cell (pH 7.4, 25° C. 50 mM Hepes); °Hemox analyzer (TES Medical Products) (pH 7.4, 37° C. 50 mM Hepes+100 mM NaCl); ▽pH7.0, 37° C.[37]; ^pH 8.5, 37° C.

Hb Prisca is a recombinant HbA with mutations β($^{S9C+C93A+C112G}$); see Fronticelli et al., *Proteins*, 2001; 44: 212-222, the entire disclosure of which is herein incorporated by reference. The polymerization of Hb Prisca is obtained through the formation of intermolecular S—S bonds between cysteine residues introduced at position β9, based on the model of Hb Porto Alegre (β9Ser to Cys; see Bonaventura and Riggs, *Science* 1967; 155: 800-802). The cysteines at β93 and β112 were replaced in order to prevent formation of spurious S—S bonds during the expression, assembly, and polymerization of the modified subunits. The final polymerization product (i.e., HB Prisca) is mainly formed by 6 to 8 tetrameric Hb molecules.

Three of the modified, non-polymerized Hb molecules against which the polymerized Hb of the invention were compared have modifications in the amino acid residues of the heme pocket. These modified, non-polymerized Hb molecules are: βL$^{28}$(B10)N, which is a recombinant HbA in which βLys$^{28}$(B10) was replaced by Asn; βV$^{67}$(E11)T, which is a recombinant HbA in which βVal$^{67}$(E11) was replaced by Thr; and αV$^{63}$(E11)T, which is a recombinant HbA in which αVal$^{63}$(E11) was replaced by Thr. See, e.g., Fronticelli et al., *Biochemistry*, 1993; 32: 1235-1242 and Pechik et al., *Biochemistry*, 1996; 35: 1935-1945, the entire disclosures of which are herein incorporated by reference. These three mutant Hb molecules have a range of oxygen affinities, as can be seen in FIG. 1.

For βL$^{28}$(B10)N, Leu$^{28}$(B10) in the B-helix of the β-chains (which is a highly conserved residue in the hydrophobic cluster on the heme distal side) was replaced with the isosteric, but more polar, asparagine. The modified residue interacts with bound $O_2$, destabilizing the T-state and increasing the oxygen affinity in this mutant Hb. Comparison of oxygen-binding curves indicated that βL$^{28}$(B10)N has a high oxygen affinity ($P_{50}$=0.64 torr) and that, in the liganded form (R-state), the affinity βL$^{28}$(B10)N for $O_2$ of is similar to that of HbA (12.5 and 13.8 torr, respectively). In the unliganded form (T-state), the $O_2$ affinity is about one order of magnitude larger in βL$^{28}$(B10)N than in HbA (0.2 and 0.03 respectively).

For βV$^{67}$(E11)T, the valine at position E11 in the E-helix of the α or β chains was replaced with the isosteric, but polar, threonine. βV$^{67}$(E11)T has a two-fold decrease in oxygen affinity ($P_{50}$=12 torr) with respect to HbA ($P_{50}$=6.5 torr), and retains a high level of cooperativity (n=2.2); see Fronticelli et al, 1993, supra. Crystallographic analysis indicated the presence of only subtle changes in the local geometry, with the presence of an H bond between the O$^\gamma$ atom of βThr$^{67}$(E11) and the backbone carbonyl of βHis$^{63}$ (E7). A water molecule was not introduced into the β-heme pocket as result of this mutation; see Pechik et al., 1996, supra. The same mutation was introduced at the same E11 site of the α-chains with different functional effects: the oxygen affinity of αV$^{62}$ (E11)T was decreased four-fold (P50=25 torr) and cooperativity was practically absent. The significantly decreased oxygen affinity measured in αV$^{62}$ (E11)T was attributed to stabilization of the water molecule present in the distal heme pocket, which becomes H-bonded to N$^{epsilon}$ of βHis$^{63}$ and O$^\gamma$ of βThr$^{67}$. This water molecule must be dissociated prior to $O_2$ bonding to the Fe-heme; see Karavitis et al., *J. Biol. Chem.* 1998; 237: 23740-23749, the entire disclosure of which is herein incorporated by reference.

Figure 2:
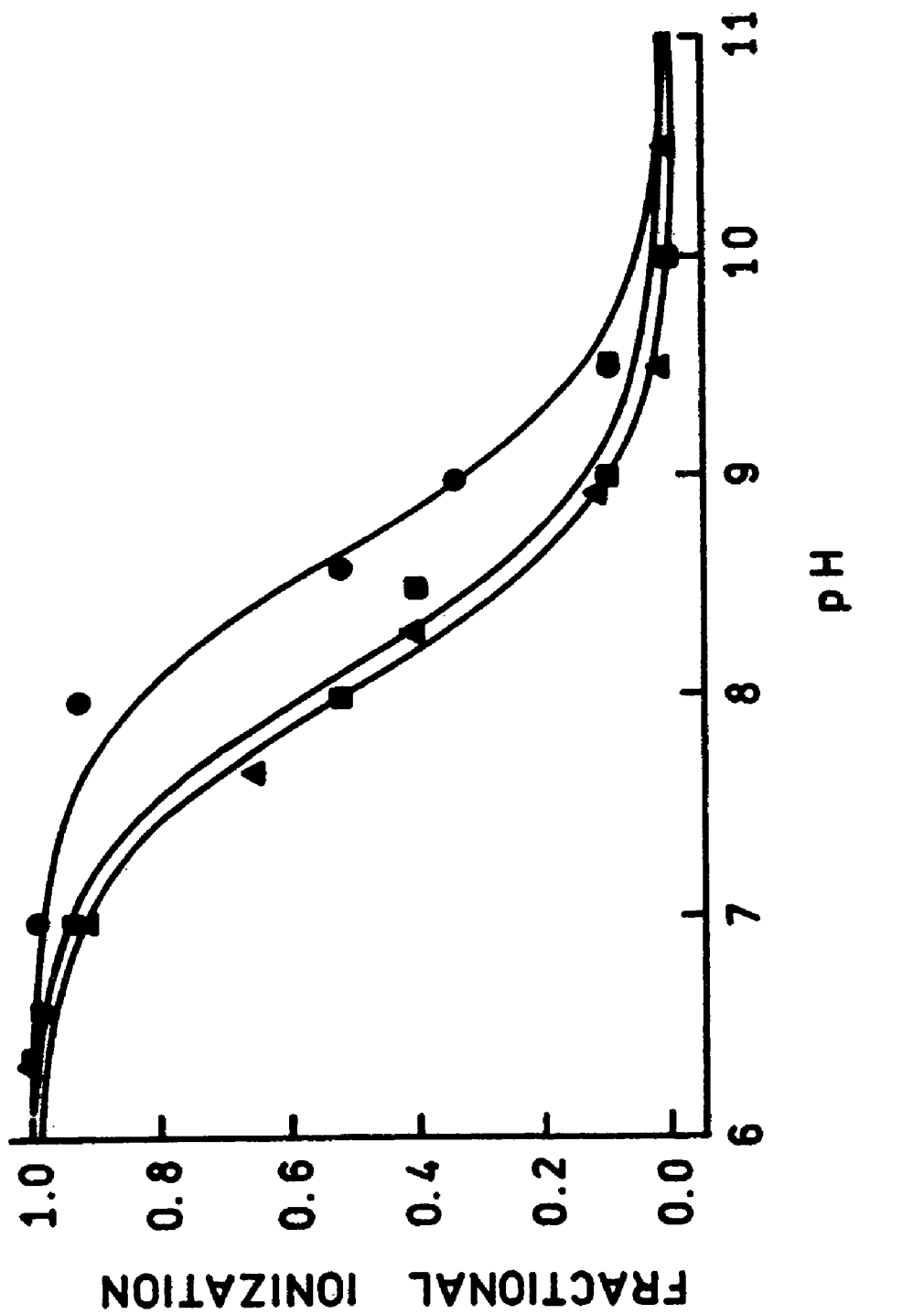
FIG. 2 is a graph showing the fractional ionization of water in the aquomet derivatives of HbA (▲); $\beta V^{67}$ (E11)T (■); $\alpha V^{63}$ (E11)T (●). Fractional changes were calculated from the deconvolution of absorption spectra recorded from 480-700 nm using aquomet HbA standards.

Inspection of the data in Table 2 indicates that increasing the heme pocket polarity increases the rate of autoxidation, as measured for the V(E11)T mutants. The stability and toxicity of a Hb-based oxygen carrier is dependent on the rate of heme loss. Thus, placing a polar residue at position E11 causes a decrease in the rate of heme transfer in βV$^{67}$(E11)T with respect to HbA; this indicates an increased heme affinity. This property should be considerably enhanced in αV$^{63}$(E11)T; see, e.g., the titration curves of the aquomet derivatives as shown in FIG. 2. These titration curves, while indicating a similar pKa of ionization of the Fe-coordinated water in HbA and βV$^{67}$(E11)T (8.2 and 8.35, respectively), show a shift to 8.7 in the pKa of αV$^{63}$(E11)T. This is consistent with the presence, in αV$^{63}$(E11)T, of a H-bond between the water molecule and O$^\gamma$ of Thr(E11), which helps to retain the heme in place. Introducing a polar residue at position E11 also causes the decrease in the half-time of NO dissociation from the heme of the mutant heme-pocket; this indicates a reduction in NO affinity in the V(E11)T mutants and a potential decrease in in vivo vasoactivity.

Three of the modified, non-polymerized Hb molecules against which the polymerized Hb of the invention were compared have modifications in the amino acid residues on the surface of the polypeptide subunits. These modified, non-polymerized Hb molecules have an intrinsically low oxygen affinity in the absence of heme pocket modifications, which is achieved through mutations that increase the hydrophobic interactions between the A-helix and the hydrophobic core of the β-subunits.

These surface-modified, non-polymerized Hb molecules are: PB4, which is a recombinant HbA with mutations β($^{V1M+H2deleted+T4I+P5A}$); and PB5, which is a recombinant HbA with mutations β($^{V1M+H2deleted+T4I+P5A+A76K}$). See Fronticelli et al., *J. Biol. Chem.* 1995; 270: 30588-30592 and Fronticelli et al., *Biophys. Chem.* 2002; 98: 115-126, the entire disclosures of which are herein incorporated by reference.

Figure 3:
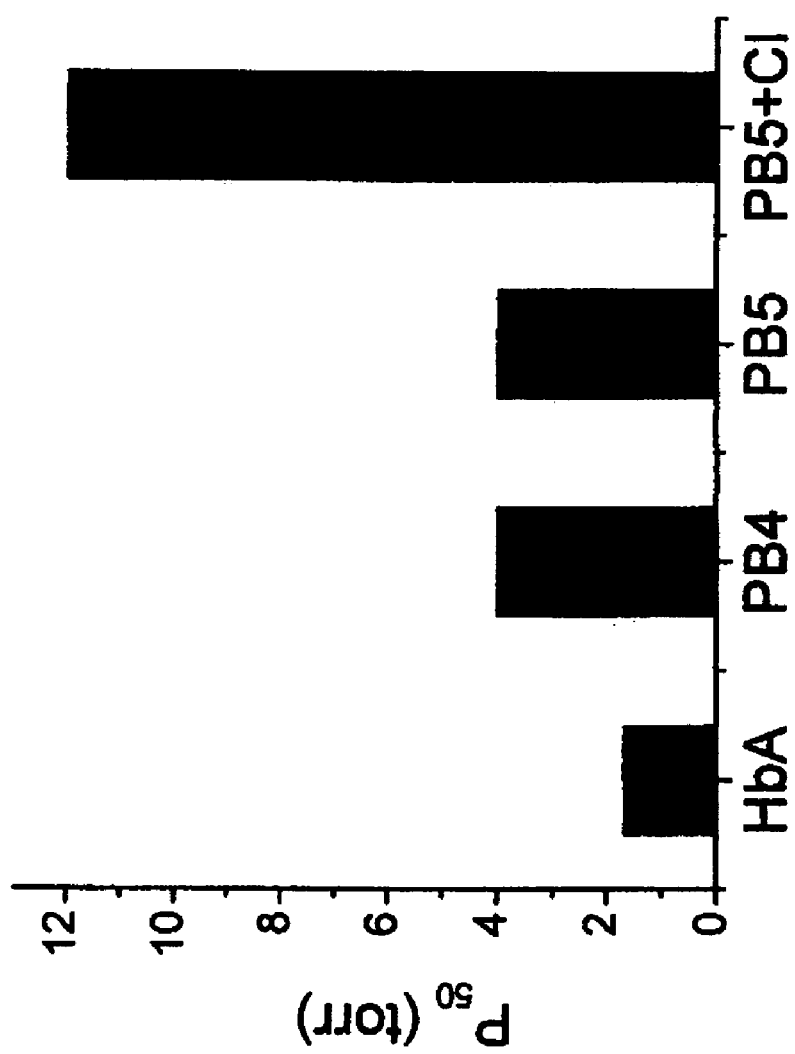
FIG. 3 is a histogram showing the partial pressure of oxygen at 50% saturation ($P_{50}$) of HbA, PB4, and PB5 at pH 7.4 in 50 mM Hepes buffer, and of PB5 at pH7.4 in Hepes buffer+100 mM NaCl. Other conditions as in FIG. 1.

PB4 has an N-terminal end similar to that of bovine Hb, and exhibits a three-fold decrease in oxygen affinity with respect to HbA (see FIG. 3 and Table 2). A regulatory mechanism whereby Cl— ions are the principal effectors stabilizing the T-state was engineered into PB4, by replacing alanine at β76 with lysine (which is the residue present at this site in bovine Hb). This mutant is designated PB5, and has an additional three-fold decrease in oxygen affinity compared to PB4 in the presence of the Cl— concentration present in the blood plasma (100 mM) (see FIG. 3 and Table 2).

The comparison of the mutant, non-polymeric Hb, normal HbA, and Hb Prisca with the polymeric Hb of the invention shown in Table 2 indicate that low oxygen affinity and high cooperativity are disadvantageous for some applications of blood substitutes. Polymers of Mb were therefore constructed, which can be used to efficiently deliver oxygen to tissues with a restricted blood flow. Moreover, a large array of Mb heme pocket mutants have been constructed and are known in the art; see, e.g., Springer et al., *Chem Rev* 1994; 94:699-714, the entire disclosure of which are herein incorporated by reference. The PolyMb of the invention, and its component monomers, can comprise any of the known Mb heme pocket mutations.

The primary amino acid structure of Mb is known. For example, the primary amino acid structure of human Mb is described in Kunishige et al., *Muscle Nerve*, 2003, 28(4), 484-492, and is presented herein as SEQ ID NO: 7. Three splice variants of the human mRNA encoding SEQ ID NO: 7 have been identified, see Kunishige et al., supra, and are provided herein as SEQ ID NO: 8 (splice variant 1), SEQ ID NO: 9 (splice variant 2) and SEQ ID NO: 10 (splice variant 3). The primary amino acid sequence of Mb from other species are also known. For example, sperm whale (*Physeter macrocephalus*) Mb amino acid sequence is described in Springer et al., *Proc. Natl. Acad. Sci. U.S.A.*, 1987, 84(24), 8961-8965, the entire disclosure of which is herein incorporated by reference, and is provided herein as SEQ ID NO: 11. The nucleic acid sequence encoding sperm whale Mb is provided herein as SEQ ID NO: 12. Domestic pig (*Sus scrofa*) Mb amino acid sequence is described in Akaboshi, *Gene*, 1985, 40(1): 137-140, the entire disclosure of which is herein incorporated by reference, and is provided herein as SEQ ID NO: 13. The nucleic acid sequence encoding pig Mb is provided herein as SEQ ID NO: 14. Bovine (*Bos taurus*) Mb amino acid sequence is described in Shimada et al., *J. Biochem.*, 1989, 105(3): 417-422, the entire disclosure of which is herein incorporated by reference, and is provided herein as SEQ ID NO: 15. The nucleic acid sequence encoding bovine Mb is provided herein as SEQ ID NO: 16.

Isolated Mb monomers of the invention can be produced by introducing polymerization sites into the molecule. These modified Mb monomers can then be polymerized by subjecting the monomers to conditions which activate the polymerization sites. A suitable technique for introducing and then activating polymerization sites on Mb monomers is described in the Examples below.

Thus, the invention provides an isolated, modified Mb monomer, wherein polymerization sites are introduced into the molecule. In a preferred embodiment, the polymerization sites are introduced into the Mb monomer by substitution of at least one, for example two or more amino acid residue with a cysteine. However, polymerization sites can also be introduced chemically; for example, with bi-functional reagents, as is known in the art. For instance, non-specific bifunctional agents can be used to cross-link the reactive amino groups of Mb monomers. Any agent that produces an intermolecular cross-link between two polypeptides such as are known in the art can be used. Suitable non-specific bi-functional agents include sebacyl chloride, aldehydes such as glutaraldehyde or polyaldehydes, diaspirin derivatives, and other bifunctional polymers such as such as PEG derivatives, inulin or dextran. See, e.g., U.S. Pat. No. 6,747,132 to Privalle et al., the entire disclosure of which is herein incorporated by reference.

Alternatively, "zero-link" technology can be used to form intermolecular cross-links between Mb monomers. For example, COOH groups on the surface of the Mb monomer can be activated, followed by a reaction of the activated COOH group with an available $NH_2$ group on the surface of another Mb monomer. See, e.g., U.S. Pat. No. 5,998,361 to Bucci et al., the entire disclosure of which is herein incorporated by reference.

In a preferred embodiment, the amino acid sequence of Mb monomers is mutated by substituting at least one, preferably two or more amino acid residues located on the surface of the folded polypeptide with a cysteine. Optionally, one or more naturally-occurring cysteines in a Mb monomer (if any) are substituted with amino acid residues which do not form intermolecular bonds. Techniques for mutating the amino acid sequence of a given polypeptide are known in the art, and are discussed in more detail below.

Any Mb molecule can be modified by introducing polymerization sites. Preferably, the modified Mb molecule comprises a sperm whale Mb molecule, although human, pig or bovine Mb molecules can be used.

One skilled in the art would understand which surface residues of a given Mb molecule can be modified to introduce a polymerization site. For example, positively charged amino acid residues such as His and/or Lys residues on the Mb monomer surface can be substituted with cysteines. Suitable residues on the surface of sperm whale Mb which can be replaced by cysteines include: Val1, Gln8, Lys50, Lys76, His12, His36, His48, His81, His113, His116, and His119. See, e.g., Yung-Hsiang et al., *Biophys. J.*, 2000, 79: 1637-1654, the entire disclosure of which is herein incorporated by reference. One skilled in the art can readily identify the analogous amino acid residues in Mb monomers from other species, for example in human, pig and bovine Mb monomers. See, e.g., Springer, *Chem. Rev.*, 1994, 94: 699-714, the entire disclosure of which is herein incorporated by reference, which states that there is qualitative agreement between analogous pig, human and sperm whale Mb heme-pocket mutants, indicating that generality of results between Mb mutants of different species can be expected.

Figure 7:
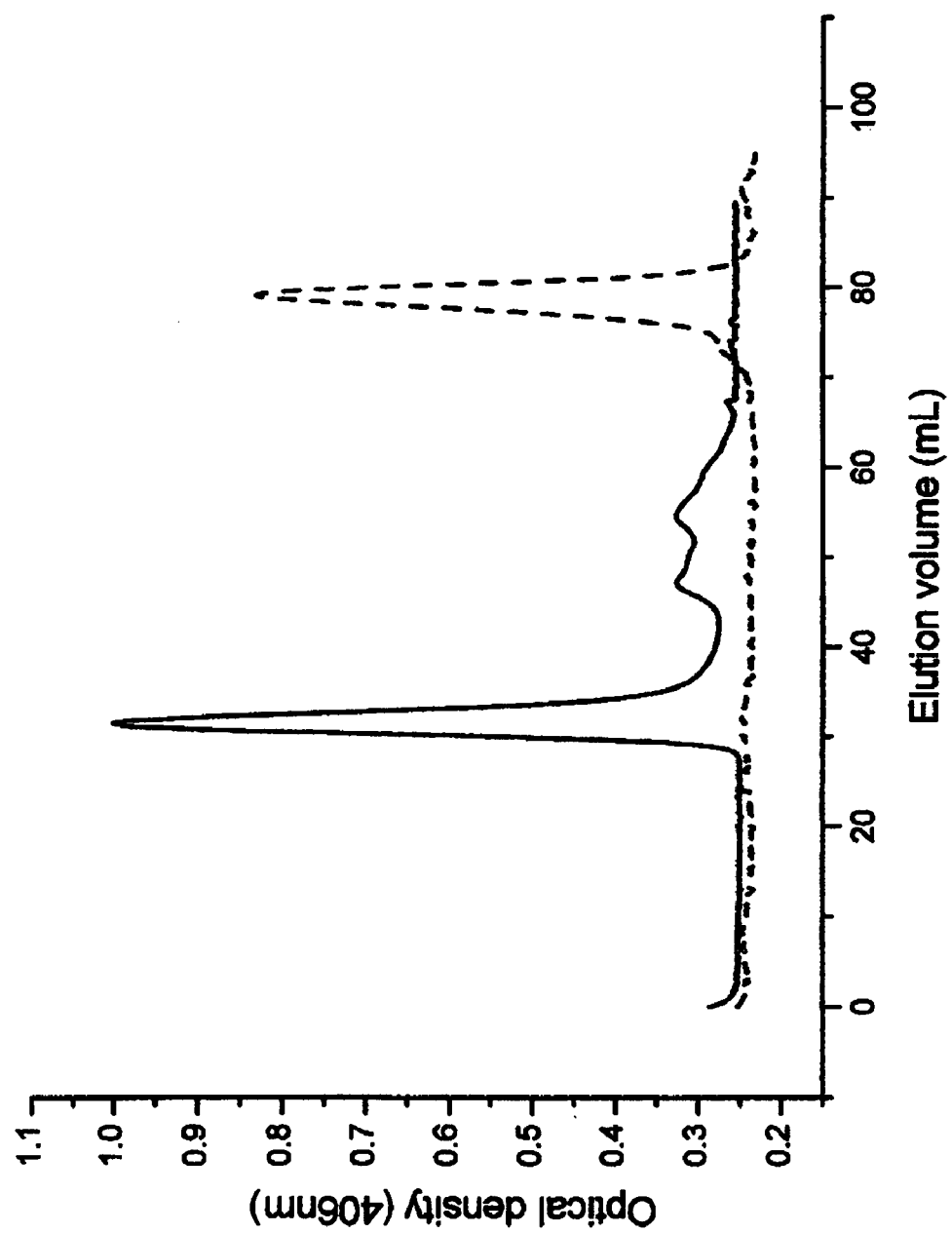
FIG. 7 is a graph showing the size exclusion chromatography of Mb (--) and PolyMb (-). Most of the PolyMb is eluted with the void volume of the column (MW 1,000 kDa). Experimental conditions as in FIG. 4.

In one embodiment, polymerization of sperm whale Mb monomers can be achieved by introducing the substitutions Gln8 to Cys, Lys50 to Cys and Lys76 to Cys. These residues are external (i.e., on the surface) of folded Mb monomers, and are in favorable reactive positions. The replacement of the lysine residues with cysteines decreases the Mb net charge, favoring intermolecular interaction and S—S bond formation. FIG. 7 shows the gel filtration chromatography of such a modified sperm whale Mb and of polymerized Mb (polyMb) made with the modified Mb monomers.

As stated above, Mb monomers of the invention can further comprise heme-pocket mutations or other which alter the oxygen affinity of the monomers. Such heme-pocket mutations and techniques for introducing them into Mb monomers are known in the art; for example, mutations to the amino acids at positions E7 (His to Gly, Gln, Ala, Val, Thr, Ile, Met, or Phe), E11 (Val to Ala, Leu, Ile, Phe, Ser, Thr, Asn, or Gln), CD1 (Phe to Val or Trp), CD4 (Phe to Leu or Val) and B10 (Leu to Ala, Val, Ile, Phe or Trp). See, e.g., Springer, 1994, supra; Carver et al., *J. Biol. Chem.*, 1994, 267, 14443-14450, and La Mar et al., *J. Biol. Chem.*, 1994, 269: 29629-29635, the entire disclosures are herein incorporated by reference.

The invention thus provides a polymer comprising polymerized Mb monomers of the invention. Preferably, the Mb polymers of the invention (also called "PolyMb") have a molecular weight of about 500 to about 1000 kilodaltons (kDa) or higher, e.g., about 1500 kDa, about 2000 kDa, about 2500 kDa or about 3000 kDa, as measured for example by size exclusion chromatography.

Polymerization does not appear to affect the ligand binding properties of Mb, as below indicated, and therefore, the vast amount of data correlating the effects of mutations on functional properties of Mbs can be utilized to tailor Mb polymers for specific clinical situations. For example, patients in septic shock can become hypertensive, in spite of massive fluid therapy and treatment with vasoconstrictor agents. In this instance, the overproduction of nitric oxide (NO) results in the lowered blood pressure. Therefore, in one embodiment, a Mb polymer of the invention (which has NO scavenging activity) can be used to treat septic shock.

In cancer, delivery of $O_2$ to the hypoxic inner core of a tumor mass increases its sensitivity to treatments such as radiotherapy and chemotherapy. Because the microvasculature of a tumor is unlike that of other tissues, sensitization through increasing $O_2$ levels requires $O_2$ be unloaded within the hypoxic core. Thus, a PolyMb of the invention that has a high oxygen affinity (denoted by a low P50 value) can be used to treat cancer, because such a PolyMb would not unload all of the bound $O_2$ before reaching the hypoxic tumor core.

As used herein, the term "oxygen affinity" refers to the avidity with which an oxygen carrier such as a heme protein binds molecular oxygen. This characteristic is defined by the oxygen equilibrium curve which relates the degree of saturation of heme protein molecules with oxygen (Y axis) with the partial pressure of oxygen (X axis). The position of this curve is denoted by the value, or "P50", which is the partial pressure of oxygen at which the oxygen carrier is half-saturated with oxygen. P50 is inversely related to oxygen affinity. The oxygen affinity of a heme protein can be measured by a variety of methods known in the art. (See, e.g., Winslow et al., J. Biol. Chem. 252(7):2331-37 (1977), the entire disclosure of which is herein incorporated by reference).

The polypeptides comprising the heme protein subunits of the invention can comprise natural or synthetic peptides produced by any known means, including synthesis by biological systems and chemical methods.

Biological synthesis of peptides is well known in the art, and includes the transcription and translation of a synthetic gene encoding the heme protein subunits, as described in more detail below. Chemical peptide synthesis includes manual and automated techniques well known to those skilled in the art.

Techniques to synthesize or otherwise obtain heme protein subunits are well known in the art. For example, automated peptide synthesis can be performed with commercially available peptide synthesizers, using conventional solid phase synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldimidazole; various active esters, e.g., esters of N-hydroxyphthalimide or N-hydroxysuccinimide; and the various cleavage reagents, e.g., trifluoroacetic acid (TFA), HCl in dioxane, boron tris-(trifluoracetate) and cyanogen bromide; and reaction in solution with isolation and purification of intermediates, are well-known to those of ordinary skill in the art.

A preferred peptide synthesis method follows conventional Merrifield solid phase procedures well known to those skilled in the art. Additional information about solid phase synthesis procedures can be had by reference to Steward and Young, Solid Phase Peptide Synthesis, W. H. Freeman & Co., San Francisco, 1969; the review chapter by Merrifield in Advances in Enzymology 32:221-296, F. F. Nold, Ed., Interscience Publishers, New York, 1969; and Erickson and Merrifield, The Proteins 2:61-64 (1990), the entire disclosures of which are herein incorporated by reference. Crude peptide preparations resulting from solid phase syntheses can be purified by methods well known in the art, such as preparative HPLC. The amino-terminus can be protected according to the methods described for example by Yang et al., FEBS Lett. 272:61-64 (1990), the entire disclosure of which is herein incorporated by reference.

Biological methods for synthesizing polypeptides comprising heme protein subunits of the invention are also within the skill in the art. For example, a nucleic acid sequence encoding the heme protein subunit can be synthesized de novo and subcloned into the appropriate expression vector for propagation in an appropriate host.

The subcloned nucleic acid sequences can be expressed directly to generate the heme protein subunit, or subjected to site-directed mutagenesis to introduce sequences coding for polymerization sites or other mutations.

Intracellularly produced heme protein subunits can be obtained from the host cell by cell lysis, or by using heterologous signal sequences fused to the protein which cause secretion of the protein into the surrounding medium. Preferably, the signal sequence is designed so that it can be removed by chemical or enzymatic cleavage. The proteins thus produced can then be purified by affinity chromatography.

The techniques used to transform cells, construct vectors, construct oligonucleotides, and perform site-specific mutagenesis are widely practiced in the art, and most practitioners are familiar with the standard resource materials which describe specific conditions and procedures. However, the following discussion is presented as a guideline for generating heme protein subunits with mutations introducing polymerization sites or other desirable characteristics, according to the present invention.

The mutant heme protein subunits of the present invention can be prepared utilizing well-known expression systems for producing recombinant heme proteins in suitable microbial hosts, such as *E. coli*. See Fronticelli et al., *J. Prot. Chem.* 10:495-501(1991), Sanna et al., *J. Biol. Chem.* 272: 3478-3486 (1996) and U.S. Pat. No. 5,239,061 to Fronticelli et al., the entire disclosures of which are incorporated herein by reference. Site-specific mutagenesis is used to introduce appropriate mutations into the native heme protein subunit nucleotide coding sequences, to provide a mutant DNA encoding the desired mutant polypeptide subunit.

Techniques of site-specific mutagenesis are within the skill in the art. The two principal techniques are the gapped duplex (A. A., Kruse, K. B., Brown, J. L. *BioTechniques* 6, 338-339, 1988) and M-13 (Zoller, M. J. and Smith, *M. Meth. Enz.* 100, 468-500, 1987) methods, the entire disclosures of which are herein incorporated by reference. Such site-directed mutageneses can be carried out using standard reagents such as the "Muta-Gene M-13 In Vitro Mutagenesis Kit" available from Bio-Rad Laboratories and used according to the manufacturer's instructions.

The modified heme proteins of the present invention can also be produced in transgenic animals. See, e.g., U.S. Pat. No. 5,922,854 to Kumar et al., the entire disclosure of which is herein incorporated by reference.

According to one embodiment of the invention, the heme protein polypeptides of the invention, including mutants thereof, are advantageously expressed as fusion proteins. The normal heme protein subunit polypeptides can be expressed, for example, as the fusion protein NS1-FX-(heme protein subunit). This fusion protein comprises 81 residues of the flu virus protein NS1, the Factor $X_a$ recognition sequence Ile-Glu-Gly-Arg (SEQ ID NO:17), and the sequence of the heme protein subunit or mutant thereof. The fusion protein can be expressed in any suitable host, for example in *E. coli* AR58 by transformation with plasmid pJKO5, the construction of which is described by Fronticelli et al., *J. Prot. Chem*, 1991, supra, the entire disclosure of which is incorporated herein by reference.

Mutants of heme protein subunits can also be prepared using the expression plasmid pNF.alpha, which is structurally analogous to pJKO5. The construction of pNF.alpha is described by Sanna et al., *J. Biol. Chem.*, 1997, supra. Expression of the plasmid in any suitable host, for example, *E. coli* strain AR120 yields large amounts of the NS1-FX-heme protein subunit fusion protein. Mutagenesis can be carried out with the appropriate mutagenizing oligonucleotides, as with pJKO5, to yield the desired heme protein subunit mutants.

The modified heme proteins of the present invention, in particular the polymerized Hb and Mb proteins, can be incorporated into physiologically acceptable blood substitute solutions, according to techniques within the skill in the art, for example as described in U.S. Pat. No. 5,028,588 to Hoffmann et al, the entire disclosure of which is herein incorporated by reference. The blood substitutes of the invention comprise at least one heme protein of the invention, for example a PolyMb, and a physiologically acceptable carrier. Suitable physiologically acceptable carriers are characterized as being sterile and non-toxic, and include water, balanced saline solution, physiologic saline solutions (e.g., Lactated Ringer's solution, Hartman's solution), dextrose solution and the like. Additional agents such as albumin, dextran and polyethylene glycol, for example in the amounts suggested in U.S. Pat. No. 5,028,588, the entire disclosure of which is herein incorporated by reference, can be added to increase oncotic pressure. Antioxidants and/or free radical scavengers such as mannitol, glutathione, ascorbic acid or vitamin E can also be included.

In one embodiment, a blood substitute solution of the invention contains from about 6 to about 120 g/L heme protein polymer, from about 135 to about 145 mEq/L sodium, from about 3.5 to about 4.5 mEq/L potassium, and from about 90 to about 100 mEq/L chloride. Preferably, the solution has a pH of about 7.3 to about 7.5, an osmolarity of about 280 to about 310, and an oncotic pressure of about 20 to about 30 mm Hg. Glucose can optionally be added to adjust the osmolarity.

The blood substitutes of the invention can be administered to a subject for any condition requiring supplementation of the oxygen-carrying capacity of the subject's blood. The amount of the blood substitute administered to a given subject will depend on the size, weight and age of the subject, the clinical condition of the subject, and the degree of impairment of the natural oxygen-carrying capacity of the subject's blood. Thus, the invention provides a method of enhancing the oxygen-carrying capacity of a subject's blood, comprising administering an effective amount of a blood substitute of the invention. As used herein, an "effective amount" of blood substitute is any amount which brings about a clinically relevant enhancement of the oxygen-carrying capacity of the subject's blood over a clinically meaningful time interval, as can be determined by the ordinarily-skilled physician. As used herein, a "subject" includes human and non-human animals.

Conditions which require supplementation of a subject's blood include trauma causing acute loss of whole blood, ischemia, hemodilution, septic shock, cancers, chronic anemia, sickle cell anemia, cardioplegia, and hypoxia.

The present blood substitutes can also be used in non-human animals, for example domestic animals such as livestock and companion animals (e.g., dogs, cats, horses, birds, reptiles), as well as other animals in aquaria, zoos, oceanaria, and other facilities that house animals. It is contemplated that the present invention finds utility in the emergency treatment of domestic and wild animals suffering a loss of blood due to injury, hemolytic anemias, and the like. For example, it is contemplated that embodiments of the present invention are useful in conditions such as equine infectious anemia, feline infectious anemia, hemolytic anemia due to chemicals and other physical agents, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic, parasitism, etc. In particular, the present invention finds use in areas where blood donors for animals of rare and/or exotic species are difficult to find.

The invention will now be illustrated with the following non-limiting examples.

EXAMPLES

Methods

For the studies of the heme pocket mutants, protein surface modifications, and HbA polymerization (Hb Prisca), the fusion protein expression systems pNFα and pJK05 were used for the α- and β-globins, respectively. See Sanna et al., *J. Biol. Chem.*, 1997, 272:3478-86 and Fronticelli et al., *J Protein Chem* 1991, 10:495-501, the entire disclosures of which are herein incorporated by reference. The advantage of these systems is that the reconstituted Hbs have only one type of chain that is recombinant, the other being isolated from native human Hb. This permits the unambiguous assignment of any modified behavior to the substitutions made in the recombinant chains. The hybrid Hb Minotaur ($\alpha_H \beta_{Bv}$) and the polymerization derivatives Hb Polytaur and Hb (Polytaur)$_n$ were expressed in a soluble form in pDLα$_H$ β$^{Bv}$ and purified as previously described (Bobofchak et al., *Am J Physiol Heart Circ Physiol*, 2003, 285:H549-61, the entire disclosure of which is herein incorporated by reference. Sperm whale Mb was expressed in pMb413, as described in Springer et al., *Proc Natl Acad Sci USA,* 1978, 84:8961-65, the entire disclosure of which is herein incorporated by reference, and purified according to the method described in Piro et al., *Biochemistry* 2001, 40:11841-50, the entire disclosure of which is herein incorporated by reference. In all of the systems used, the mutations introduced were verified by DNA sequencing. The rate constant $O_2$ dissociation from Mb and PolyMb was determined using the oxygen pulse method as described in Gibson et al., *Proc Natl Acad Sci USA,* 1973, 70:1-4, the entire disclosure of which is herein incorporated by reference. The rate constant $O_2$ and CO binding was determined by photolysis as described in Springer et al., 1978, supra, using the instrument described by Arcovito et al., *J Biol Chem,* 2001, 276:41073-79, the entire disclosure of which is herein incorporated by reference. Transfusion experiments were conducted as previously described (Bobofchak et al., 2003, supra). All procedures were approved by the relevant institutional animal care and use committees.

A cysteine residue was introduced into Hb Minotaur at position β9 without the substitution of the natural cysteines present at α112 and β93 as described in Bobofchak et al., 2003, supra. This mutant was polymerized to form Hb (Polytaur)$_n$, which was a heterogeneous polymer with components having MW of 1,000 kDa or higher, as seen in size exclusion chromatography shown in FIG. 4. Oxygen-binding measurements indicated that Hb (Polytaur)$_n$ had oxygen-binding characteristics similar to Mb; i.e., high oxygen affinity (P50=about 2.0 torr) and loss of cooperativity (n=1). See Table 2, supra.

A mouse model was used to determine the effect of the Hb polymers Hb Polytaur, Hb (Polytaur)$_n$ and the chemically polymerized bovine Hb ZL-HbBv on arterial blood pressure following hypervolemic exchange as described in (Bobofchak et al., 2003, supra). The infarct volume (±SE) after 2 h focal cerebral ischemia was measured in control mice with no transfusion, and in mice transfused with either 5% albumin, 3% Hb Polytaur ($P_{50}$=16.0 torr, n=1.7), 3% Hb (Polytaur)$_n$ ($P_{50}$=2.0 torr, n=1.0) 0, or 6% ZL-HbBv ($P_{50}$=4.0 torr, n=1.0). The results are presented in FIG. 5. The small increase in blood pressure observed in the three Hb groups is probably related to moderate hypervolemia after hypervolumetric exchange transfusion.

Figure 5:
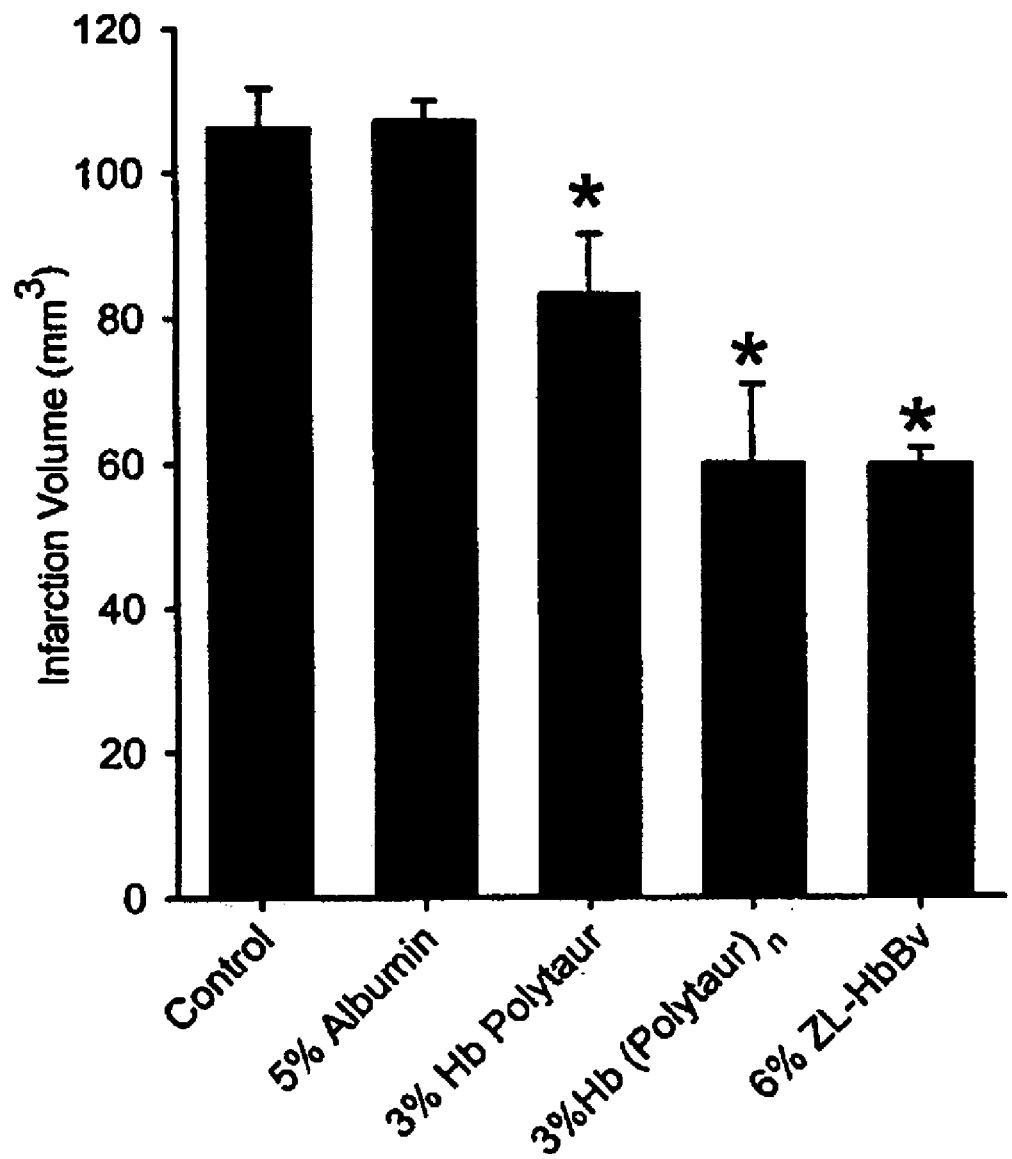
FIG. 5 is a histogram showing the infarct volume (±SE) after 2 h focal cerebral ischemia in control mice with no transfusion, and in mice transfused with either 5% albumin, 3% Hb Polytaur ($P_{50}$=16.0 torr, n=1.7), 3% Hb (Polytaur)$_n$ ($P_{50}$=2.0 torr, n=1.0) 0, or 6% ZL-HbBv ($P_{50}$=4.0 torr, n=1.0). *P<0.05 from control and albumin groups by ANOVA and Newman-Keuls test.
Figure 6:
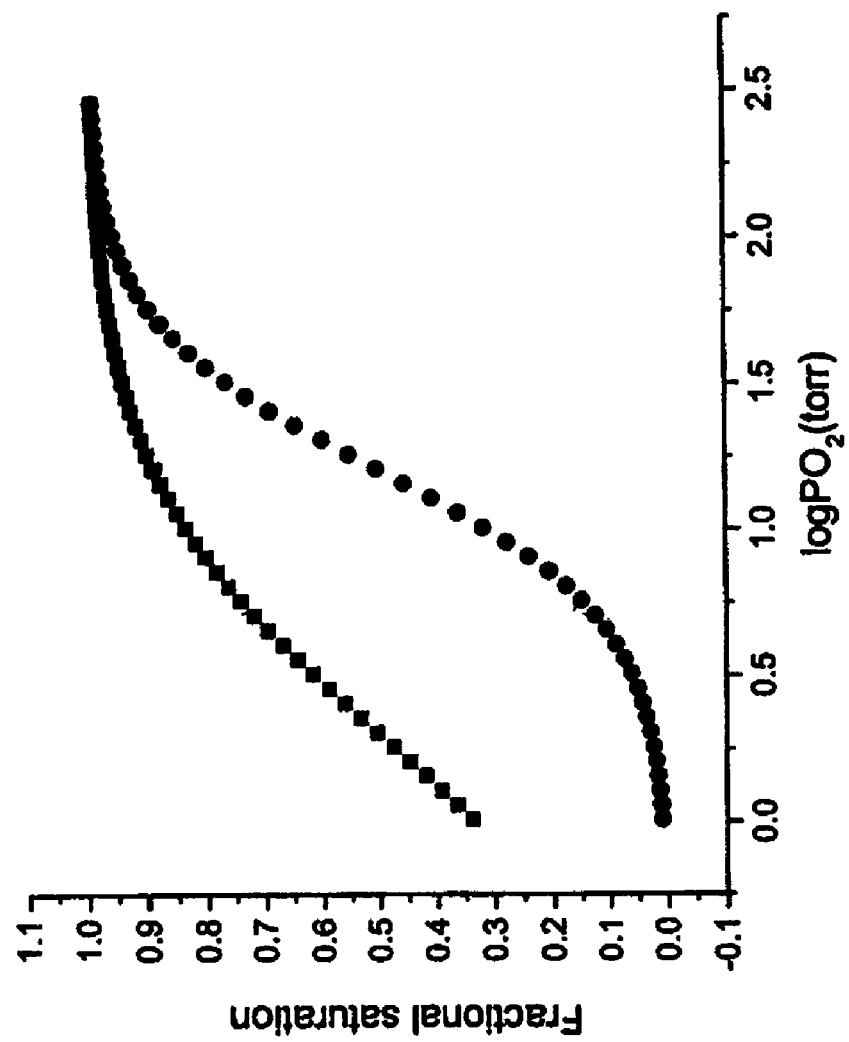
FIG. 6 is a graph showing the fractional saturation with oxygen binding of Hb Polytaur(●) and Hb (Polytaur)$_n$ (■) in 50 mM Hepes buffer+100 mM NaCl at pH 7.4. T=37° C.

The effect of polymeric Hbs on transient cerebral ischemia was also investigated, as described in Bobofchak et al., 2003, supra and Nemoto et al., *J Cereb Blood Flow Metab,* 2003; Suppl 1; 23:48, the entire disclosure of which is herein incorporated by reference. FIG. 5 shows the reduction in infarct volume following middle cerebral artery occlusion (MCAO). An exchange transfusion was performed over a 20-min period starting at 10 min after MCAO. Infarct volume was reduced by 20% by 3% Hb Polytaur (P50=17.0, n=1.7); by 40% by 3% Hb (Polytaur)$_n$ (P50=−2.0; n=1) and by 40% by 6% ZL-HbBv (P50=−4.0; n=1). These results indicated that Hbs with a low P50 and no cooperativity preferentially unloaded $O_2$ in ischemic tissue, even at low plasma concentrations. A rationale for this phenomenon is presented in FIG. 6, where the fractional saturation of Hb Polytaur and Hb (Polytaur)$_n$ with $O_2$ is compared. These data indicated that at very low partial pressure of $O_2$, (5.0-6.0 torr), as in hypoxic/ischemic tissues, Hb (Polytaur)$_n$ still released $O_2$, whereas Hb Polytaur was nearly completely deoxygenated.

Figure 8A:
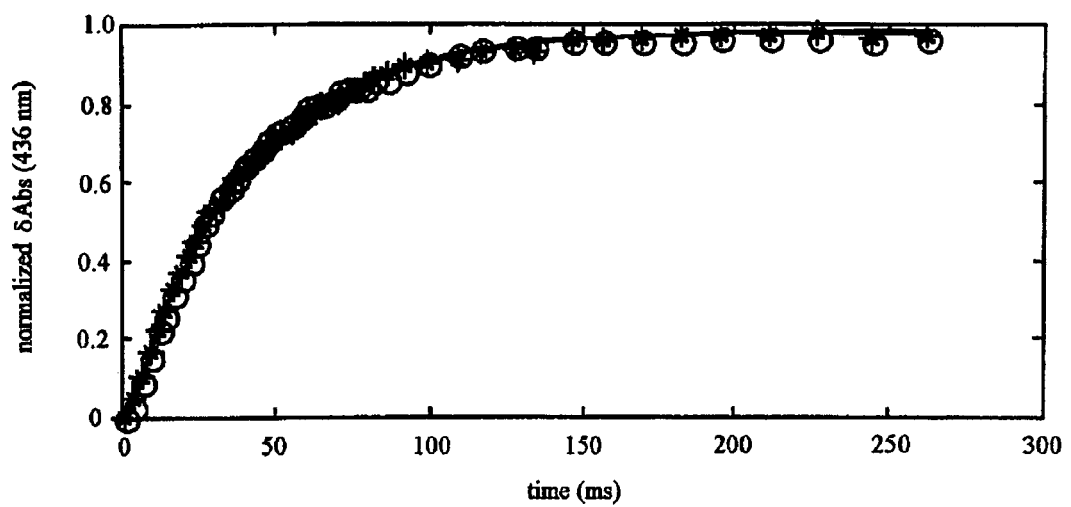
FIG. 8 shows the normalized time courses of oxygen dissociation from Mb and from a combination with Mb and PolyMb. A: Normalized time course of oxygen dissociation from MbO$_2$ (asterisks) and PolyMbO$_2$ (circles). Continuous lines represent the best fit of the experimental data to a single exponential. Observation wavelength: 436 nm; Buffer: 0.05 M Tris with 0.1 M NaCl. PH 7.2; temperature 23° C. B: Normalized time course of combination to Mb and PolyMb as observed after laser flash photolysis. Symbols and experimental conditions as in FIG. 8A.
Figure 8B:
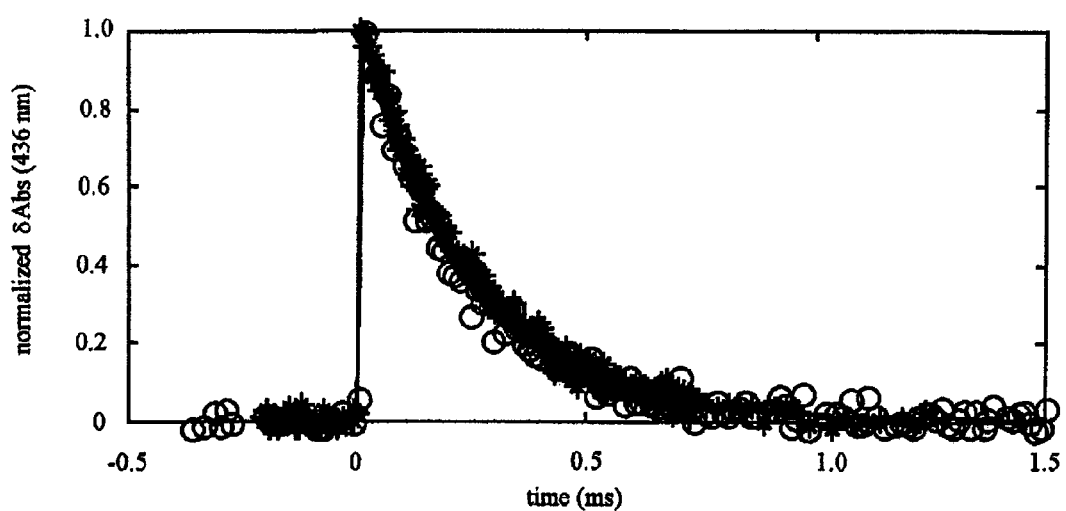

The normalized time course for oxygen dissociation from Mb $O_2$ is shown in FIG. 8A. The normalized time course for the recombination of 0.27 mM $O_2$ with 4.0 μM Mb or PolyMb following photolysis by a 5 ns laser flash, is shown in FIG. 8B. The observed time courses were fitted to a single exponential; the quality of the fit demonstrated that PolyMb behaved homogeneously with respect to $O_2$ combination and dissociation, and very similarly to Mb. Thus, polymerization did not alter these properties. The calculated kinetic rate constants are listed in Table 3, together with the calculated affinity constants.

The photochemical method was used to determine the rate constant of CO combination at 1.0 mM CO and 4.0 μM Mb or PolyMb (Table 3). Also in this case, Mb and PolyMb behaved similarly; i.e., the time course of CO recombination conformed to a single exponential with the same rate constant for both proteins, thus confirming the conclusion derived from the experiments on $MbO_2$.

TABLE 3

| Protein | $k'_{O2}$ ($\times 10$ $M^{-6}s^{-1}$) | $k_{O2}s^{-1}$ | K ($\times 10$ $M^{-6}$) | $P_{50(torr)}$ | $k'_{CO}$ ($\times 10$ $M^{-6}s^{-1}$) |
|---|---|---|---|---|---|
| Mb | 15.0 | 27.0 | 0.55 | 1.1 | 4.0 |
| PolyMb | 15.0 | 27.0 | 0.55 | 1.1 | 4.0 |

All documents referenced in this application are herein incorporated by reference in their entirety. A variety of modifications to the embodiments described above will be apparent to those skilled in the art from the disclosure provided herein. Thus, the invention may be embodied in other specific forms without departing from the spirit or essential attributes thereof.

We claim:

1. An isolated hemoglobin comprising a first and a second polypeptide, each having the amino acid sequence of the normal human hemoglobin alpha chain, and a third and fourth polypeptide, each having the sequence of normal bovine hemoglobin beta chain, wherein at least one polypeptide comprises at least one mutation which introduces a polymerization site.

2. The isolated hemoglobin of claim 1, wherein the at least one mutation which introduces a polymerization site is the substitution of the alanine at position 9 for cysteine on at least one of the polypeptides having the sequence of normal bovine hemoglobin beta chain.

3. The isolated hemoglobin of claim 2, wherein the at least one mutation further comprises substitution of the naturally ocurring cysteine residues with an amino acid residue which is not cysteine.

4. The isolated hemoglobin of claim 1, wherein the naturally ocurring cysteines are substituted with alanines.

5. The isolated hemoglobin of claim 1, wherein at least one of the polypeptides having the amino acid sequence of the normal human hemoglobin alpha chain comprises a mutation of residue 104 from cysteine to serine, and wherein at least one of the polypeptides having the amino acid sequence of the normal bovine hemoglobin beta chain comprises a mutation of residue 9 from alanine to cysteine and a mutation of residue 93 from cysteine to alanine.

6. The isolated hemoglobin of claim 1, wherein at least one of the polypeptides having the amino acid sequence of the normal bovine hemoglobin beta chain comprises a mutation of residue 9 from alanine to cysteine.

7. A polymer comprising the isolated hemoglobin of claim 1.

8. A polymer comprising the isolated hemoglobin of claim 5.

9. A polymer comprising the isolated hemoglobin of claim 6.

10. The polymer of claim 9, wherein the polymer has a molecular weight at least 1000 kilodaltons.

11. A nucleic acid comprising a nucleotide sequence which encodes a polypeptide having the amino acid sequence of the normal human hemoglobin alpha chain modified with a mutation of residue 104 from cysteine to serine.

12. A nucleic acid comprising a nucleotide sequence which encodes a polypeptide having the amino acid sequence of the normal bovine hemoglobin beta chain modified with a mutation of residue 9 from alanine to cysteine and a mutation of residue 93 from cysteine to alanine.

13. A nucleic acid comprising a nucleotide sequence which encodes a polypeptide having the amino acid sequence of the normal bovine hemoglobin beta chain modified with a mutation of residue 9 from alanine to cysteine.

14. A polypeptide encoded by the nucleic acid of claim 11.

15. A polypeptide encoded by the nucleic acid of claim 12.

16. A polypeptide encoded by the nucleic acid of claim 13.

17. A blood substitute comprising the isolated hemoglobin of claim 1, or a polymer thereof.

18. A blood substitute comprising the isolated hemoglobin of claim 5, or a polymer thereof.

19. A blood substitute comprising the isolated hemoglobin of claim 6, or a polymer thereof.

20. The isolated hemoglobin of claim 1, wherein at least one of the alpha chain polypeptides or at least one of the beta chain polypeptides further comprises a modification to the heme binding pocket.

21. The isolated hemoglobin of claim 20, wherein the modification to the heme pocket comprises a mutation that alters the oxygen affinity of the hemoglobin.

22. The isolated hemoglobin of claim 21, wherein the oxygen affinity is higher than the oxygen affinity of whole blood.

23. An isolated hybrid hemoglobin comprising at least one human hemoglobin subunit polypeptide and at least one non-human mammalian hemoglobin subunit polypeptide.

24. The isolated hybrid hemoglobin of claim 23, comprising two human hemoglobin alpha subunit polypeptides, and two non-human mammalian hemoglobin subunit polypeptides.

25. A method of producing the isolated hemoglobin of claim 1, comprising modifying at least one subunit polypeptide to introduce a polymerization site.

26. A method of supplementing the oxygen-carrying capacity of a subject's blood, comprising administering to the patient an effective amount of the blood substitute comprising an isolated hemoglobin or a polymer thereof, wherein the isolated hemoglobin comprises a first and a second polypeptide, each having the amino acid sequence of the normal human hemoglobin alpha chain, and a second and third polypeptide, each having the sequence of normal bovine hemoglobin beta chain, and wherein at least one polypeptide comprises at least one mutation which introduces a polymerization site.

* * * * *

SEQUENCE LISTING

```
<160> NUMBER OF SEQ ID NOS: 35

<210> SEQ ID NO 1
<211> LENGTH: 98
<212> TYPE: PRT
<213> ORGANISM: Homo sapiens

<400> SEQUENCE: 1

Pro His Phe Asp Leu Ser His Gly Ser Ala Gln Val Lys Gly His Gly
 1               5                  10                  15

Lys Lys Val Ala Asp Ala Leu Thr Asn Ala Val Ala His Val Asp Asp
            20                  25                  30

Met Pro Asn Ala Leu Ser Ala Leu Ser Asp Leu His Ala His Lys Leu
        35                  40                  45
```

```
Arg Val Asp Pro Val Asn Phe Lys Leu Leu Ser His Cys Leu Leu Val
    50                  55                  60

Thr Leu Ala Ala His Leu Pro Ala Glu Phe Thr Pro Ala Val His Ala
65                  70                  75                  80

Ser Leu Asp Lys Phe Leu Ala Ser Val Ser Thr Val Leu Thr Ser Lys
                85                  90                  95

Tyr Arg

<210> SEQ ID NO 2
<211> LENGTH: 147
<212> TYPE: PRT
<213> ORGANISM: Homo sapiens

<400> SEQUENCE: 2

Met Val His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 3
<211> LENGTH: 575
<212> TYPE: DNA
<213> ORGANISM: Homo sapiens

<400> SEQUENCE: 3
actcttctgg tccccacaga ctcagagaga acccaccatg gtgctgtctc ctgccgacaa      60
gaccaacgtc aaggccgcct ggggcaaggt tggcgcgcac gctggcgagt atggtgcgga    120
ggccctggag aggatgttcc tgtccttccc caccaccaag acctacttcc cgcacttcga    180
cctgagccac ggctctgccc aggttaaggg ccacggcaag aagtggcgc acgcgctgac    240 caacgccgtg gcgcacgtgg acgacatgcc caacgcgctg tccgccctga gcgacctgca    300
cgcgcacaag cttcggggtgg acccggtcaa cttcaagctc ctaagccact gcctgctggt    360
gaccctggcc gcccacctcc ccgccgagtt caccctgcg gtgcacgcct ccctggacaa    420
gttcctggct tctgtgagca ccgtgctgac ctccaaatac cgttaagctg agcctcggt    480 agcagttcct cctgccagat gggcctccca acgggccctc ctcccctcct tgcaccggcc    540
cttcctggtc tttgaataaa gtctgagtgg gcggc                                575
```

<210> SEQ ID NO 4
<211> LENGTH: 626
<212> TYPE: DNA
<213> ORGANISM: Homo sapiens

<400> SEQUENCE: 4

```
acatttgctt ctgacacaac tgtgttcact agcaacctca aacagacacc atggtgcatc      60
tgactcctga ggagaagtct gccgttactg ccctgtgggg caaggtgaac gtggatgaag     120
ttggtggtga ggccctgggc aggctgctgg tggtctaccc cttggacccag aggttctttg    180
agtcctttgg ggatctgtcc actcctgatg ctgttatggg caaccctaag gtgaaggctc     240
atggcaagaa agtgctcggt gcctttagtg atggcctggc tcacctggac aacctcaagg     300
gcacctttgc cacactgagt gagctgcact gtgacaagct gcacgtggat cctgagaact     360
tcaggctcct gggcaacgtg ctggtctgtg tgctggccca tcactttggc aaagaattca     420
ccccaccagt gcaggctgcc tatcagaaag tggtggctgg tgtggctaat gccctggccc     480
acaagtatca ctaagctcgc tttcttgctg tccaatttct attaaaggtt cctttgttcc     540
ctaagtccaa ctactaaact gggggatatt atgaagggcc ttgagcatct ggattctgcc     600
taataaaaaa catttatttt cattgc                                         626
```

<210> SEQ ID NO 5
<211> LENGTH: 145
<212> TYPE: PRT
<213> ORGANISM: Bos taurus

<400> SEQUENCE: 5

```
Met Leu Thr Ala Glu Glu Lys Ala Ala Val Thr Ala Phe Trp Gly Lys
  1               5                  10                  15
Val Lys Val Asp Glu Val Gly Gly Glu Ala Leu Gly Arg Leu Leu Val
                 20                  25                  30
Val Tyr Pro Trp Thr Gln Arg Phe Phe Glu Ser Phe Gly Asp Leu Ser
             35                  40                  45
Thr Ala Asp Ala Val Met Asn Asn Pro Lys Val Lys Ala His Gly Lys
         50                  55                  60
Lys Val Leu Asp Ser Phe Ser Asn Gly Met Lys His Leu Asp Asp Leu
 65                  70                  75                  80
Lys Gly Thr Phe Ala Ala Leu Ser Glu Leu His Cys Asp Lys Leu His
                 85                  90                  95
Val Asp Pro Glu Asn Phe Lys Leu Leu Gly Asn Val Leu Val Val Val
            100                 105                 110
Leu Ala Arg Asn Phe Gly Lys Glu Phe Thr Pro Val Leu Gln Ala Asp
        115                 120                 125
Phe Gln Lys Val Val Ala Gly Val Ala Asn Ala Leu Ala His Arg Tyr
    130                 135                 140
His
145
```

<210> SEQ ID NO 6
<211> LENGTH: 2072
<212> TYPE: DNA
<213> ORGANISM: Bos taurus

<400> SEQUENCE: 6

```
tttaatagca atttgtattg ctggaatgac tgtgatctag agatgcccag aaagagggct      60
gatggtctaa agtcagtgcc aggaagacca aggagagcta tgactatcat cgttcaagcc     120
```

```
tcaccctgtg gaaccacaac ttggcatgag caatctgctc acagaagcag ggagggcagg      180
aggcagggct gggcataaaa ggaagagctg ggccagctgc tgcttacact tgcttctgac      240
acaaccgtgt tcactagcaa ctacacaaac agacaccatg ctgactgctg aggagaaggc      300
tgccgtcacc gccttttggg gcaaggtgaa agtggatgaa gttggtggtg aggccctggg      360
caggtaggta tcccacttac aaggcaggtt taaggagagt gaaatgcacc tgggcgtgtg      420
aggacagagc cgtccctgag attcagagag ctgctggctt cctctgacct tgtgctgttt      480
tctcccccta ggctgctggt tgtctacccc tggactcaga ggttctttga gtcctttggg      540
gacttgtcca ctgctgatgc tgttatgaac aaccctaagg tgaaggccca tggcaagaag      600
gtgctagatt cctttagtaa tggcatgaag catctcgatg acctcaaggg caccttttgct     660 gcgctgagtg agctgcactg tgataagctg catgtggatc ctgagaactt caaggtgagt      720
ttgtggaatc ctcagtgttc tccttcttct ttttatggtc aagctcatgt catgaggaga      780
aagctgaatg caggacaca gtttagaatg gagaagaggg attctggtta gattactaag       840
gactcctcag aaccgtttag actcttttaa cctctttgtt cacaaccagt atttcctctg      900
attcattctt gttctctgtt gtctgcaatg tcctcttttt aattatattt tttattttga      960
gggtttaatt tgaaaaaaaa attatatatc aactttaaaa attgtatcta atatttcccc     1020
cttatctgtt cctttcaagg aataagatgt tctattgctt tttgaaatga ttcaaaataa     1080 taaaataat aacaagttct ggattaagtt agaaagagag aaacatttct aaatatatat      1140
tcgggaagat ataggtagat tcacatcagt agtaacaact tcacttcagt catctttgtg     1200
cttatatcta cggtcacagc ttgggataag actgaaatac cctgaatcta accttggatt     1260
tccctcatag ctcagttggt taagcatctg cctgcaatgc aagagatccc agttcgattc     1320
ctgggtcggg aaggatggct ggagaaggga taggcaccca ctccagtatt cttgggtttc     1380
ccttgtggct cagctggtaa agaatctgcc tgcaatgtgg gagacccagc ttctatccct     1440
gagtttggaa gatcccctgg agaagggaaa ggctacccac tccagtattc tggcctggag     1500
aaatctatgg actgtagagt catggggttg caaagaatca gacacgattg agagactctc     1560
acttcactca cctgcactaa ccctgccctt gcttaatgtc ttttccacac agctcctggg     1620
caacgtgcta gtggttgtgc tggctcgcaa ttttggcaag gaattcaccc cggtgctgca     1680
ggctgacttt cagaaggtgg tggctggtgt ggccaatgcc ctggcccaca gatatcatta     1740
agctcccttt cctgctttcc aggaaaggtt ttttcatcct cagagcccaa agattgaata     1800
tggaaaaatt atgaagtgtt ttgagcatct ggcctctgcc taataaagac atttattttc     1860
attgcactgg tgtatttaaa ttatttcact gtctcttact cagatgggca catgggaggg     1920
caaaacactg aagacataaa gaaatgaagg gctagtcgag accttgagaa aatatatcag     1980
tatcttggac cccatgacag cagtggttgt aaatagctga tgttatggaa aacaggcttt     2040
gctccttagc cttactctcc cttaaagaat tc                                    2072
```

<210> SEQ ID NO 7
<211> LENGTH: 154
<212> TYPE: PRT
<213> ORGANISM: Homo sapiens

<400> SEQUENCE: 7

```
Met Gly Leu Ser Asp Gly Glu Trp Gln Leu Val Leu Asn Val Trp Gly
 1               5                  10                  15

Lys Val Glu Ala Asp Ile Pro Gly His Gly Gln Glu Val Leu Ile Arg
            20                  25                  30
```

Leu Phe Lys Gly His Pro Glu Thr Leu Glu Lys Phe Asp Lys Phe Lys
         35                  40                  45

His Leu Lys Ser Glu Asp Glu Met Lys Ala Ser Glu Asp Leu Lys Lys
 50                  55                  60

His Gly Ala Thr Val Leu Thr Ala Leu Gly Gly Ile Leu Lys Lys Lys
65                   70                  75                  80

Gly His His Glu Ala Glu Ile Lys Pro Leu Ala Gln Ser His Ala Thr
                 85                  90                  95

Lys His Lys Ile Pro Val Lys Tyr Leu Glu Phe Ile Ser Glu Cys Ile
             100                 105                 110

Ile Gln Val Leu Gln Ser Lys His Pro Gly Asp Phe Gly Ala Asp Ala
         115                 120                 125

Gln Gly Ala Met Asn Lys Ala Leu Glu Leu Phe Arg Lys Asp Met Ala
    130                 135                 140

Ser Asn Tyr Lys Glu Leu Gly Phe Gln Gly
145                 150

<210> SEQ ID NO 8
<211> LENGTH: 1078
<212> TYPE: DNA
<213> ORGANISM: Homo sapiens

<400> SEQUENCE: 8
gcagcctcaa acccccagctg ttggggccag acacccagt gagcccatac ttgctctttt      60
tgtcttcttc agactgcgcc atgggctca gcgacgggga tggcagttg gtgctgaacg     120 tctgggggaa ggtggaggct gacatcccag ccatgggca ggaagtcctc atcaggctct     180
ttaagggtca cccagagact ctggagaagt ttgacaagtt caagcacctg aagtcagagg     240
acgagatgaa ggcgtctgag gacttaaaga agcatggtgc caccgtgctc accgccctgg     300
gtggcatcct taagaagaag gggcatcatg aggcagagat taagcccctg gcacagtcgc     360
atgccaccaa gcacaagatc cccgtgaagt acctggagtt catctcggaa tgcatcatcc     420
aggttctgca gagcaagcat cccggggact tggtgctga tgcccagggg gccatgaaca     480
aggccctgga gctgttccgg aaggacatgg cctccaacta caaggagctg ggcttccagg     540
gctaggcccc tgccgctccc acccccaccc atctgggccc cgggttcaag agagagcggg     600
gtctgatctc gtgtagccat atagagtttg cttctgagtg tctgctttgt ttagtagagg     660
tgggcaggag gagctgaggg gctgggggctg ggtgttgaa gttggctttg catgcccagc     720
gatgcgcctc cctgtgggat gtcatcaccc tgggaaccgg gagtggccct ggctcactg     780 tgttctgcat ggtttggatc tgaattaatt gtcctttctt ctaaatccca accgaacttc     840
ttccaacctc caaactggct gtaaccccaa atccaagcca ttaactacac ctgacagtag     900
caattgtctg attaatcact ggcccttga agacagcaga atgtcccttt gcaatgagga     960
ggagatctgg gctgggcggg ccagctgggg aagcatttga ctatctggaa cttgtgtgtg    1020
cctcctcagg tatggcagtg actcacctgg ttttaataaa acaacctgca acatctca     1078

<210> SEQ ID NO 9
<211> LENGTH: 1170
<212> TYPE: DNA
<213> ORGANISM: Homo sapiens

<400> SEQUENCE: 9
gagcatgttg gcctggtcct ttgctaggta ctgtagagca ggtgagagag tgagggggaa      60

|     |     |
| --- | --- |
| ggactccaaa ttagaccagt tcttagccat gaagcagaga ctctgaagcc agactacctg | 120 |
| ggtcccaatc ttgggcttgg tatttcctcg ctgtgtgact ctggactgcg ccatggggct | 180 |
| cagcgacggg gaatggcagt tggtgctgaa cgtctggggg aaggtggagg ctgacatccc | 240 |
| aggccatggg caggaagtcc tcatcaggct ctttaagggt cacccagaga ctctggagaa | 300 |
| gtttgacaag ttcaagcacc tgaagtcaga ggacgagatg aaggcgtctg aggacttaaa | 360 |
| gaagcatggt gccaccgtgc tcaccgccct gggtggcatc cttaagaaga aggggcatca | 420 |
| tgaggcagag attaagcccc tggcacagtc gcatgccacc aagcacaaga tccccgtgaa | 480 |
| gtacctggag ttcatctcgg aatgcatcat ccaggttctg cagagcaagc atcccgggga | 540 |
| ctttggtgct gatgcccagg ggccatgaa caaggccctg agctgttcc ggaaggacat | 600 |
| ggcctccaac tacaaggagc tgggcttcca gggctaggcc cctgccgctc caccccac | 660 |
| ccatctgggc cccgggttca agagagagcg gggtctgatc tcgtgtagcc atatagagtt | 720 |
| tgcttctgag tgtctgcttt gtttagtaga ggtgggcagg aggagctgag gggctggggc | 780 |
| tggggtgttg aagttggctt tgcatgccca gcgatgcgcc tccctgtggg atgtcatcac | 840 |
| cctgggaacc gggagtggcc cttggctcac tgtgttctgc atggtttgga tctgaattaa | 900 |
| ttgtcctttc ttctaaatcc caaccgaact tcttccaacc tccaaactgg ctgtaacccc | 960 |
| aaatccaagc cattaactac acctgacagt agcaattgtc tgattaatca ctggcccctt | 1020 |
| gaagacagca gaatgtccct tgcaatgag gaggagatct gggctgggcg ggccagctgg | 1080 |
| ggaagcattt gactatctgg aacttgtgtg tgcctcctca ggtatggcag tgactcacct | 1140 |
| ggttttaata aaacaacctg caacatctca | 1170 |

<210> SEQ ID NO 10
<211> LENGTH: 1153
<212> TYPE: DNA
<213> ORGANISM: Homo sapiens

<400> SEQUENCE: 10

|     |     |
| --- | --- |
| aatggcacct gccctaaaat agcttcccat gtgagggcta gagaaaggaa aagattagac | 60 |
| cctccctgga tgagagagag aaagtgaagg agggcagggg aggggacag cgagccattg | 120 |
| agcgatcttt gtcaagcatc ccagaagact gcgccatggg gctcagcgac ggggaatggc | 180 |
| agttggtgct gaacgtctgg gggaaggtgg aggctgacat cccaggccat gggcaggaag | 240 |
| tcctcatcag gctctttaag ggtcacccag agactctgga agtttgac aagttcaagc | 300 |
| acctgaagtc agaggacgag atgaaggcgt ctgaggactt aaagaagcat ggtgccaccg | 360 |
| tgctcaccgc cctgggtggc atccttaaga agaaggggca tcatgaggca gagattaagc | 420 |
| ccctggcaca gtcgcatgcc accaagcaca agatccccgt gaagtacctg gagttcatct | 480 |
| cggaatgcat catccaggtt ctgcagagca agcatcccgg gactttggt gctgatgccc | 540 |
| aggggccat gaacaaggcc ctgagctgt tccggaagga catggcctcc aactacaagg | 600 |
| agctgggctt ccagggctag gcccctgccg ctcccacccc cacccatctg gccccgggt | 660 |
| tcaagagaga gcgggtctg atctcgtgta gccatataga gtttgcttct gagtgtctgc | 720 |
| tttgtttagt agaggtgggc aggaggagct gaggggctgg ggctggggtg ttgaagttgg | 780 |
| cttttgcatgc ccagcgatgc gcctccctgt gggatgtcat caccctggga accgggagtg | 840 |
| gcccttggct cactgtgttc tgcatggttt ggatctgaat taattgtcct tcttctaaa | 900 |
| tcccaaccga acttcttcca acctccaaac tggctgtaac cccaaatcca agccattaac | 960 |
| tacacctgac agtagcaatt gtctgattaa tcactggccc cttgaagaca gcagaatgtc | 1020 |

```
cctttgcaat gaggaggaga tctgggctgg gcgggccagc tggggaagca tttgactatc    1080
tggaacttgt gtgtgcctcc tcaggtatgg cagtgactca cctggtttta ataaaacaac    1140
ctgcaacatc tca                                                       1153
```

<210> SEQ ID NO 11
<211> LENGTH: 154
<212> TYPE: PRT
<213> ORGANISM: Physeter macrocephalus

<400> SEQUENCE: 11

```
Met Val Leu Ser Glu Gly Glu Trp Gln Leu Val Leu His Val Trp Ala
 1               5                  10                  15

Lys Val Glu Ala Asp Val Ala Gly His Gly Gln Asp Ile Leu Ile Arg
            20                  25                  30

Leu Phe Lys Ser His Pro Glu Thr Leu Glu Lys Phe Asp Arg Phe Lys
        35                  40                  45

His Leu Lys Thr Glu Ala Glu Met Lys Ala Ser Glu Asp Leu Lys Lys
    50                  55                  60

His Gly Val Thr Val Leu Thr Ala Leu Gly Ala Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Glu Ala Ile
            100                 105                 110

Ile His Val Leu His Ser Arg His Pro Gly Asn Phe Gly Ala Asp Ala
        115                 120                 125

Gln Gly Ala Met Asn Lys Ala Leu Glu Leu Phe Arg Lys Asp Ile Ala
    130                 135                 140

Ala Lys Tyr Lys Glu Leu Gly Tyr Gln Gly
145                 150
```

<210> SEQ ID NO 12
<211> LENGTH: 507
<212> TYPE: DNA
<213> ORGANISM: Artificial Sequence
<220> FEATURE:
<223> OTHER INFORMATION: Physeter macrocephalus (sperm whale) synthetic
     myoglobin gene

<400> SEQUENCE: 12

```
ctgcagataa ctaactaaag gagaacaaca acaatggttc tgtctgaagg tgaatggcag     60
ctggttctgc atgtttgggc taaagttgaa gctgacgtcg ctggtcatgg tcaggacatc    120
ttgattcgac tgttcaaatc tcatccggaa actctgaaaa attcgatcg tttcaaacat     180 ctgaaaactg aagctgaaat gaaagcttct gaagatctga aaaaacatgg tgttaccgtg    240
ttaactgccc taggtgctat ccttaagaaa aagggcatc atgaagctga gctcaaaccg    300
cttgcgcaat cgcatgctac taaacataag atcccgatca aatacctgga attcatctct    360
gaagcgatca tccatgttct gcattctaga catccaggta cttcggtgc tgacgctcag    420 ggtgctatga caaagctctc gagctgttc cgtaaagata tcgctgctaa gtacaaagaa    480
ctgggttacc agggttaatg aggtacc                                        507
```

<210> SEQ ID NO 13
<211> LENGTH: 154
<212> TYPE: PRT
<213> ORGANISM: Sus scrofa

<400> SEQUENCE: 13

```
Met Gly Leu Ser Asp Gly Glu Trp Gln Leu Val Leu Asn Val Trp Gly
  1               5                  10                  15
Lys Val Glu Ala Asp Val Ala Gly His Gly Gln Glu Val Leu Ile Arg
                 20                  25                  30
Leu Phe Lys Gly His Pro Glu Thr Leu Glu Lys Phe Asp Lys Phe Lys
             35                  40                  45
His Leu Lys Ser Glu Asp Glu Met Lys Ala Ser Glu Asp Leu Lys Lys
         50                  55                  60
His Gly Asn Thr Val Leu Thr Ala Leu Gly Gly Ile Leu Lys Lys Lys
 65                  70                  75                  80
Gly His His Glu Ala Glu Leu Thr Pro Leu Ala Gln Ser His Ala Thr
                 85                  90                  95
Lys His Lys Ile Pro Val Lys Tyr Leu Glu Phe Ile Ser Glu Ala Ile
                100                 105                 110
Ile Gln Val Leu Gln Ser Lys His Pro Gly Asp Phe Gly Ala Asp Ala
            115                 120                 125
Gln Gly Ala Met Ser Lys Ala Leu Glu Leu Phe Arg Asn Asp Met Ala
        130                 135                 140
Ala Lys Tyr Lys Glu Leu Gly Phe Gln Gly
145                 150
```

<210> SEQ ID NO 14
<211> LENGTH: 1111
<212> TYPE: DNA
<213> ORGANISM: Sus scrofa

<400> SEQUENCE: 14

```
cagagccagg acacccagta cgcccgcact tgctctgttt ctcttctgca gactgtgcca      60
tggggctcag cgacggggaa tggcagctgg tgctgaacgt ctgggggaag gtggaggctg     120
atgtcgcagg ccatgggcag gaggtcctca tcaggctctt aagggtcacc ccgagaccc     180
tggagaaatt tgacaagttt aagcacctga gtcagagga tgagatgaag gcctctgagg     240
acctgaagaa gcacggcaac acggtgctga ctgccctggg gggcatcctt aagaagaagg     300
ggcatcatga ggcagagctg acgcccctgg cccaatcgca tgccaccaag cacaagatcc     360
ctgtcaagta cctggagttc atctcagaag ccatcatcca ggttctgcag agcaagcatc     420
ctggggactt tggtgctgac gcccagggag ccatgagcaa ggccctggaa ctcttccgga     480
acgacatggc ggccaagtac aaggagctgg gcttccaggg ctaagccccc cagacgcccc     540
tcacccaccc atccacttgg gccagggccc ccgcggaggg tgggcgctg aagctcctgt     600
agctgtaggg tttgcttctg agtgttgctt tgttcatgag aggtgggtgg agaggtgga     660
ggggctggtg gtggtggtgg gggggtgttc aggtggtttc acgtgcggcg ggggcaggg     720
aggttgaggg gtgggggga ccaggttttc tgcggagggt catcaccctg ggaaccgggt     780
gaagcatggc ttggctcact gtggccccca gagtttaggt ccaacttaac ccacctctcc     840
ccgaaatgcc agcacagtcc ctgccagcct ccaaaccgac ccgcgccttc ctccccgcct     900
tgaatcacca atcaagctgt aaccctaaac tccagccata actctctgat catcactttg     960
aagacagcag aacgtcccct tagccccggga aggaggcgtg gcagggtgg acagtcaca    1020
cccagctcct gggaggcgtg gtgtctggaa cctaagtacc ttgcaggtga cggatgacgc    1080
acccggtttt aataaaagac tccgcactgt c                                  1111
```

<210> SEQ ID NO 15
<211> LENGTH: 154
<212> TYPE: PRT
<213> ORGANISM: Bos taurus

<400> SEQUENCE: 15

```
Met Gly Leu Ser Asp Gly Glu Trp Gln Leu Val Leu Asn Ala Trp Gly
 1               5                  10                  15

Lys Val Glu Ala Asp Val Ala Gly His Gly Gln Glu Val Leu Ile Arg
                20                  25                  30

Leu Phe Thr Gly His Pro Glu Thr Leu Glu Lys Phe Asp Lys Phe Lys
            35                  40                  45

His Leu Lys Thr Glu Ala Glu Met Lys Ala Ser Glu Asp Leu Lys Lys
        50                  55                  60

His Gly Asn Thr Val Leu Thr Ala Leu Gly Gly Ile Leu Lys Lys Lys
 65                 70                  75                  80

Gly His His Glu Ala Glu Val Lys His Leu Ala Glu Ser His Ala Asn
                85                  90                  95

Lys His Lys Ile Pro Val Lys Tyr Leu Glu Phe Ile Ser Asp Ala Ile
               100                 105                 110

Ile His Val Leu His Ala Lys His Pro Ser Asp Phe Gly Ala Asp Ala
           115                 120                 125

Gln Ala Ala Met Ser Lys Ala Leu Glu Leu Phe Arg Asn Asp Met Ala
       130                 135                 140

Ala Gln Tyr Lys Val Leu Gly Phe His Gly
145                 150
```

<210> SEQ ID NO 16
<211> LENGTH: 1077
<212> TYPE: DNA
<213> ORGANISM: Bos taurus

<400> SEQUENCE: 16

```
cagctgtcgg agacagacac ccagtcagtc ccgcccttgt tcttttttctc ttcttcagac    60
tgcgccatgg ggctcagcga cggggaatgg cagttggtgc tgaatgcctg ggggaaggtg   120
gaggctgatg tcgcaggcca tgggcaggag gtcctcatca ggctcttcac aggtcatccc   180
gagaccctgg agaaatttga caagttcaag cacctgaaga cagaggctga gatgaaggcc   240
tccgaggacc tgaagaagca tggcaacacg gtgctcacgg ccctgggggg tatcctgaag   300
aaaaagggtc accatgaggc agaggtgaag cacctggccg agtcacatgc caacaagcac   360
aagatccctg tcaagtacct ggagttcatc tcggacgcca tcatccatgt tctacatgcc   420
aagcatcctt cagacttcgg tgctgatgcc caggctgcca tgagcaaggc cctggaactg   480
ttccggaatg acatggctgc ccagtacaag gtgctgggct ccatggctaa gccccaccc   540
ctgtgcccct caccccaccc acctgggcag ggtgggcggg actgaatcc caagtagtta   600
tagggtttgc ttctgagtgt gtgctttgtt taggagaggt gggtggaaga ggtggatggg   660
ttaggggtgg agggagcctt gggagaggcc tgggaccag gctttcagtg gagggtgcat   720
caacttggga accatgagaa gcttgactgt ggctggctga gtctgggtca aactcaactt   780
tcctttcacc tcaatgccaa cccaattcct accaacctct aaactgacct gcacctttac   840
cctcaccctta aatccccaat ccgagctgtc aacataaact ccagcctaat tctctgaccc   900
catcacccag ccccttgaag acagcagagt gtcttgcttg ccctgagaag gaagtgtggg   960
ccgggtggga cggccacacc cagccctagg gaggcatgga ggcatggtgt ctgcaacata  1020
```
aatgtccctt ctcaggtagg ggagtgacac ctggtttaat aaaggatttc tcacatc        1077

<210> SEQ ID NO 17
<211> LENGTH: 4
<212> TYPE: PRT
<213> ORGANISM: Artificial Sequence
<220> FEATURE:
<223> OTHER INFORMATION: Factor Xa recognition sequence

<400> SEQUENCE: 17

Ile Glu Gly Arg
 1

<210> SEQ ID NO 18
<211> LENGTH: 142
<212> TYPE: PRT
<213> ORGANISM: Rattus norvegicus

<400> SEQUENCE: 18

Met Val Leu Ser Ala Asp Asp Lys Thr Asn Ile Lys Asn Cys Trp Gly
 1               5                  10                  15

Lys Ile Gly Gly His Gly Gly Glu Tyr Gly Glu Glu Ala Leu Gln Arg
            20                  25                  30

Met Phe Ala Ala Phe Pro Thr Thr Lys Thr Tyr Phe Ser His Ile Asp
        35                  40                  45

Val Ser Pro Gly Ser Ala Gln Val Lys Ala His Gly Lys Lys Val Ala
    50                  55                  60

Asp Ala Leu Ala Lys Ala Ala Asp His Val Glu Asp Leu Pro Gly Ala
65                  70                  75                  80

Leu Ser Thr Leu Ser Asp Leu His Ala His Lys Leu Arg Val Asp Pro
                85                  90                  95

Val Asn Phe Lys Phe Leu Ser His Cys Leu Leu Val Thr Leu Ala Cys
            100                 105                 110

His His Pro Gly Asp Phe Thr Pro Ala Met His Ala Ser Leu Asp Lys
        115                 120                 125

Phe Leu Ala Ser Val Ser Thr Val Leu Thr Ser Lys Tyr Arg
    130                 135                 140

<210> SEQ ID NO 19
<211> LENGTH: 556
<212> TYPE: DNA
<213> ORGANISM: Rattus norvegicus

<400> SEQUENCE: 19
acattctcct tctgatagac tcaggaagca atcatggtgc tctctgcaga tgacaaaacc        60
aacatcaaga actgctgggg gaagattggt ggccatggtg gtgaatatgg cgaggaggcc       120
ctacagagga tgttcgctgc cttccccacc accaagacct acttctctca cattgatgta       180
agccccggct ctgcccaggt caaggctcac ggcaagaagg ttgctgatgc cttggccaaa       240
gctgcagacc acgtcgaaga cctgcctggt gccctgtcca ctctgagcga cctgcatgcc       300
cacaaactgc gtgtggatcc tgtcaacttc aagttcctga gccactgcct gctggtgacc       360
ttggcttgcc accaccctgg agatttcaca cccgccatgc acgcctctct ggacaaattc       420
cttgcctctg tgagcactgt gctgacctcc aagtaccgtt aagccgcctc ctgccgggct       480
tgccttctga ccaggccctt cttccctccc ttgcacctat acctcttggt ctttgaataa       540
agcctgagta ggaagc                                                       556

<210> SEQ ID NO 20
<211> LENGTH: 147
<212> TYPE: PRT
<213> ORGANISM: Rattus norvegicus

<400> SEQUENCE: 20

Met Val His Leu Thr Asp Ala Glu Lys Ala Val Asn Gly Leu Trp
1               5                   10                  15

Gly Lys Val Asn Pro Asp Asp Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Pro Lys Val Lys Ala His
    50                  55                  60

Gly Lys Lys Val Ile Asn Ala Phe Asn Asp Gly Leu Lys His Leu Asp
65              70                  75                  80

Asn Leu Lys Gly Thr Phe Ala His Leu Ser Glu Leu His Cys Asp Lys
                85                  90                  95

Leu His Val Asp Pro Glu Asn Phe Arg Leu Leu Gly Asn Met Ile Val
            100                 105                 110

Ile Val Leu Gly His His Leu Gly Lys Glu Phe Thr Pro Cys Ala Gln
        115                 120                 125

Ala Ala Phe Gln Lys Val Val Ala Gly Val Ala Ser Ala Leu Ala His
    130                 135                 140

Lys Tyr His
145

<210> SEQ ID NO 21
<211> LENGTH: 620
<212> TYPE: DNA
<213> ORGANISM: Rattus norvegicus

<400> SEQUENCE: 21
tgcttctgac atagttgtgt tgactcacaa actcagaaac agacaccatg gtgcacctga      60
ctgatgctga aaggctgct gttaatggcc tgtggggaaa ggtgaaccct gatgatgttg     120
gtggcgaggc cctgggcagg ctgctggttg tctaccttg acccagagg tactttgata      180 gctttgggga cctgtcctct gcctctgcta tcatgggtaa ccctaaggtg aaggcccatg     240
gcaagaaggt gataaacgcc ttcaatgatg gcctgaaaca cttggacaac ctcaagggca     300
cctttgctca tctgagtgaa ctccactgtg acaagctgca tgtggatcct gagaacttca     360
ggctcctggg caatatgatt gtgattgtgt tgggccacca cctgggcaag gaattcaccc     420
cctgtgcaca ggctgccttc cagaaggtgg tggctggagt ggccagtgcc ctggctcaca     480
agtaccacta aacctctttt cctgctcttg tctttgtgca atggtcaatt gttcccaaga     540
gagcatctgt cagttgttgt caaaatgaca aagacctttg aaaatctgtc ctactaataa     600
aaggcattta ctttcactgc                                                 620

<210> SEQ ID NO 22
<211> LENGTH: 142
<212> TYPE: PRT
<213> ORGANISM: Mus musculus

<400> SEQUENCE: 22

Met Val Leu Ser Gly Glu Asp Lys Ser Asn Ile Lys Ala Ala Trp Gly
1               5                   10                  15

```
Lys Ile Gly Gly His Gly Ala Glu Tyr Gly Ala Glu Ala Leu Glu Arg
            20                  25                  30

Met Phe Ala Ser Phe Pro Thr Lys Thr Tyr Phe Pro His Phe Asp
        35                  40                  45

Val Ser His Gly Ser Ala Gln Val Lys Gly His Gly Lys Lys Val Ala
 50                  55                  60

Asp Ala Leu Ala Ser Ala Ala Gly His Leu Asp Asp Leu Pro Gly Ala
 65                  70                  75                  80

Leu Ser Ala Leu Ser Asp Leu His Ala His Lys Leu Arg Val Asp Pro
                 85                  90                  95

Val Asn Phe Lys Leu Leu Ser His Cys Leu Leu Val Thr Leu Ala Ser
            100                 105                 110

His His Pro Ala Asp Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140

<210> SEQ ID NO 23
<211> LENGTH: 564
<212> TYPE: DNA
<213> ORGANISM: Mus musculus

<400> SEQUENCE: 23
cacttctgat tctgacagac tcaggaagaa accatggtgc tctctgggga agacaaaagc      60
aacatcaagg ctgcctgggg gaagattggt ggccatggtg ctgaatatgg agctgaagcc     120
ctggaaagga tgtttgctag cttccccacc accaagacct actttcctca ctttgatgta     180
agccacggct ctgcccaggt caagggtcac ggcaagaagg tcgccgatgc gctggccagt     240
gctgcaggcc acctcgatga cctgcccggt gccttgtctg ctctgagcga cctgcatgcc     300
cacaagctgc gtgtggatcc cgtcaacttc aagctcctga ccactgcct gctggtgacc      360 ttggctagcc accaccctgc cgatttcacc ccgcggtac atgcctctct ggacaaattc      420
cttgcctctg tgagcaccgt gctgacctcc aagtaccgtt aagctgcctt ctgcggggct     480
tgccttctgg ccatgccctt cttctctccc ttgcacctgt acctcttggt ctttgaataa     540
agcctgagta ggaagaagcc tgca                                             564

<210> SEQ ID NO 24
<211> LENGTH: 147
<212> TYPE: PRT
<213> ORGANISM: Mus musculus

<400> SEQUENCE: 24

Met Val His Leu Thr Asp Ala Glu Lys Ala Ala Val Ser Gly Leu Trp
 1               5                  10                  15

Gly Lys Val Asn Ala Asp Glu Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Ala Lys Val Lys Ala His
 50                  55                  60

Gly Lys Lys Val Ile Thr Ala Phe Asn Asp Gly Leu Asn His Leu Asp
 65                  70                  75                  80

Ser Leu Lys Gly Thr Phe Ala Ser Leu Ser Glu Leu His Cys Asp Lys
                 85                  90                  95

Leu His Val Asp Pro Glu Asn Phe Arg Leu Leu Gly Asn Met Ile Val
```

-continued

```
                100                 105                 110
Ile Val Leu Gly His His Leu Gly Lys Asp Phe Thr Pro Ala Ala Gln
            115                 120                 125
Ala Ala Phe Gln Lys Val Val Ala Gly Val Ala Ala Leu Ala His
        130                 135                 140
Lys Tyr His
145
```

<210> SEQ ID NO 25
<211> LENGTH: 630
<212> TYPE: DNA
<213> ORGANISM: Mus musculus

<400> SEQUENCE: 25

| | |
|---|---:|
| gtttacgttt gcttctgatt ctgttgtgtt gacttgcaac ctcagaaaca gacatcatgg | 60 |
| tgcacctgac tgatgctgag aaggctgctg tctctggcct gtggggaaag gtgaacgccg | 120 |
| atgaagttgg tggtgaggcc ctgggcaggc tgctggttgt ctacccttgg acccagcggt | 180 |
| actttgatag ctttggagac ctatcctctg cctctgctat catgggtaat gccaaagtga | 240 |
| aggcccatgg caagaaagtg ataactgcct ttaacgatgg cctgaatcac ttggacagcc | 300 |
| tcaagggcac ctttgccagc ctcagtgagc tccactgtga caagctgcat gtggatcctg | 360 |
| agaacttcag gctcctgggc aatatgatcg tgattgtgct gggccaccac ctgggcaagg | 420 |
| atttcacccc cgctgcacag gctgccttcc agaaggtggt ggctggagtg gctgctgccc | 480 |
| tggctcacaa gtaccactaa gccccttttc tgctattgtc tatgcacaaa ggttatatgt | 540 |
| cccctagaga aaaactgtca attgtgggga atgatgaag cctttgggc atctagcttt | 600 |
| tatctaataa atgatattta ctgtcatccc | 630 |

<210> SEQ ID NO 26
<211> LENGTH: 147
<212> TYPE: PRT
<213> ORGANISM: Mus musculus

<400> SEQUENCE: 26

```
Met Val His Leu Thr Asp Ala Glu Lys Ser Ala Val Ser Cys Leu Trp
1               5                   10                  15
Ala Lys Val Asn Pro Asp Glu Val Gly Gly Glu Ala Leu Gly Arg Leu
            20                  25                  30
Leu Val Val Tyr Pro Trp Thr Gln Arg Tyr Phe Asp Ser Phe Gly Asp
        35                  40                  45
Leu Ser Ser Ala Ser Ala Ile Met Gly Asn Pro Lys Val Lys Ala His
    50                  55                  60
Gly Lys Lys Val Ile Thr Ala Phe Asn Glu Gly Leu Lys Asn Leu Asp
65                  70                  75                  80
Asn Leu Lys Gly Thr Phe Ala Ser Leu Ser Glu Leu His Cys Asp Lys
                85                  90                  95
Leu His Val Asp Pro Glu Asn Phe Arg Leu Leu Gly Asn Ala Ile Val
            100                 105                 110
Ile Val Leu Gly His His Leu Gly Lys Asp Phe Thr Pro Ala Ala Gln
        115                 120                 125
Ala Ala Phe Gln Lys Val Val Ala Gly Val Ala Thr Ala Leu Ala His
    130                 135                 140
```

Lys Tyr His
145

<210> SEQ ID NO 27
<211> LENGTH: 632
<212> TYPE: DNA
<213> ORGANISM: Mus musculus

<400> SEQUENCE: 27

| | | | | | |
|---|---|---|---|---|---|
| gttgtgttga | cttgcaactt | cagaaacaga | catcatggtg | cacctgactg | atgctgagaa | 60 |
| gtctgctgtc | tcttgcctgt | gggcaaaggt | gaacccgat | gaagttggtg | gtgaggccct | 120 |
| gggcaggctg | ctggttgtct | acccttggac | ccagcggtac | tttgatagct | ttggagacct | 180 |
| atcctctgcc | tctgctatca | tgggtaatcc | caaggtgaag | gcccatggca | aaaggtgat | 240 |
| aactgccttt | aacgagggcc | tgaaaaacct | ggacaacctc | aagggcaccct | ttgccagcct | 300 |
| cagtgagctc | cactgtgaca | agctgcatgt | ggatcctgag | aacttcaggc | tcctgggcaa | 360 |
| tgcgatcgtg | attgtgctgg | ccaccaccct | gggcaaggat | ttcacccctg | ctgcacaggc | 420 |
| tgccttccag | aaggtggtgg | ctggagtggc | cactgccctg | gctcacaagt | accactaagc | 480 |
| ccctttctg | ctattgtcta | tgcacaaagg | ttatatgtcc | cctagagaaa | aactgtcaag | 540 |
| tgtggggaaa | tgatgaagac | ctttgggcat | ctagcttta | tctaataaat | gatatttact | 600 |
| gtcatctcaa | aaaaaaaaaa | aaaaaaaaaa | aa | | | 632 |

<210> SEQ ID NO 28
<211> LENGTH: 142
<212> TYPE: PRT
<213> ORGANISM: Bos taurus

<400> SEQUENCE: 28

Met Val Leu Ser Ala Ala Asp Lys Gly Asn Val Lys Ala Ala Trp Gly
1               5                   10                  15

Lys Val Gly Gly His Ala Ala Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Ala Lys Val Ala
    50                  55                  60

Ala Ala Leu Thr Lys Ala Val Glu His Leu Asp Asp Leu Pro Gly Ala
65                  70                  75                  80

Leu Ser Glu Leu Ser Asp Leu His Ala Tyr Lys Leu Arg Val Asp Pro
                85                  90                  95

Val Asn Phe Lys Leu Leu Ser His Ser Leu Leu Val Thr Leu Ala Ser
            100                 105                 110

His Leu Pro Ser Asp Phe Thr Pro Ala Val His Ala Ser Leu Asp Lys
        115                 120                 125

Phe Leu Ala Asn Val Ser Thr Val Leu Thr Ser Lys Tyr Arg
    130                 135                 140

<210> SEQ ID NO 29
<211> LENGTH: 706
<212> TYPE: DNA
<213> ORGANISM: Bos taurus

<400> SEQUENCE: 29
atggtgctgt ctgccgccga caagggcaat gtcaaggccg cctggggcaa ggttggcggc     60

-continued

```
cacgctgcag agtatggcgc agaggccctg gagaggtgag caccgcactt gccccgaggg      120
gaccgggccg cacgccgggc gcgtccttgt cccgggccgc tcggcctaag cccggctttc      180
ccgcctcttc acccaggatg ttcctgagct tccccaccac caagacctac ttcccccact      240
tcgacctgag ccacggctcc gcgcaggtca agggccacgg cgcgaaggtg gccgccgcgc      300
tgaccaaagc ggtggaacac ctggacgacc tgcccggtgc cctgtctgaa ctgagtgacc      360
tgcacgctta aagctgcgt gtggacccgg tcaacttcaa ggtgagctcg cgggcagggc      420
cgggacagat ctgggctagc ggggcagaga atgcggcggc cccccaccc agccccccgcc      480 cccctgacgt cccctctctc ggcagcttct gagccactcc ctgctggtga ccctggcctc      540
ccacctcccc agtgatttca ccccccgcggt ccacgcctcc ctggacaagt tcttggccaa      600
cgtgagcacc gtgctgacct ccaaataccg ttaagctgga gcctcggcga cccctaccct      660
ggcctggagc ccccttgcgc tctgcgcact ctcacctcct gatctt                    706
```

<210> SEQ ID NO 30
<211> LENGTH: 142
<212> TYPE: PRT
<213> ORGANISM: Bos taurus

<400> SEQUENCE: 30

```
Met Val Leu Ser Ala Ala Asp Lys Gly Asn Val Lys Ala Ala Trp Gly
 1               5                  10                  15

Lys Val Gly Gly His Ala Ala Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Ala Lys Val Ala
    50                  55                  60

Ala Ala Leu Thr Lys Ala Val Glu His Leu Asp Asp Leu Pro Gly Ala
65                  70                  75                  80

Leu Ser Glu Leu Ser Asp Leu His Ala His Lys Leu Arg Val Asp Pro
                85                  90                  95

Val Asn Phe Lys Leu Leu Ser His Ser Leu Leu Val Thr Leu Ala Ser
            100                 105                 110

His Leu Pro Ser Asp Phe Thr Pro Ala Val His Ala Ser Leu Asp Lys
        115                 120                 125

Phe Leu Ala Ser Val Ser Thr Val Leu Thr Ser Lys Tyr Arg
    130                 135                 140
```

<210> SEQ ID NO 31
<211> LENGTH: 706
<212> TYPE: DNA
<213> ORGANISM: Bos taurus

<400> SEQUENCE: 31

```
atggtgctgt ctgccgccga caagggcaat gtcaaggccg cctggggcaa ggttggcggc       60
cacgctgcag agtatggcgc agaggccctg gagaggtgag caccgcactt gccccgaggg      120
gaccgggccg cacgccgggc gcgtccttgt cccgggccgc tcggcctaag cccggctttc      180
ccgcctcttc acccaggatg ttcctgagct tccccaccac caagacctac ttcccccact      240
tcgacctgag ccacggctcc gcgcaggtca agggccacgg cgcgaaggtg gccgccgcgc      300
tgaccaaagc ggtggaacac ctggacgacc tgcccggtgc cctgtctgaa ctgagtgacc      360
```

```
tgcacgctca caagctgcgt gtggacccgg tcaacttcaa ggtgagctcg cgggcagggc      420
cgggacagat ctgggctagc ggggcagaga atgcggcggc gccccaccc agccccgcc       480 cccctgacgt ccctctctc ggcagcttct gagccactcc ctgctggtga ccctggcctc       540
ccacctcccc agtgatttca ccccgcggt ccacgcctcc ctggacaagt tcttggccag       600
cgtgagcacc gtgctgacct ccaaataccg ttaagctgga gccttggcga ccctacccct     660
ggcctggagc cccttgcgc tctgcgcact ctcacctcct gatctt                      706
```

<210> SEQ ID NO 32
<211> LENGTH: 142
<212> TYPE: PRT
<213> ORGANISM: Bos taurus

<400> SEQUENCE: 32

```
Met Val Leu Ser Ala Ala Asp Lys Gly Asn Val Lys Ala Ala Trp Gly
 1               5                  10                  15

Lys Val Gly Gly His Ala Ala Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Ala Lys Val Ala
    50                  55                  60

Ala Ala Leu Thr Lys Ala Val Glu His Leu Asp Asp Leu Pro Gly Ala
65                  70                  75                  80

Leu Ser Glu Leu Ser Asp Leu His Ala His Lys Leu Arg Val Asp Pro
                85                  90                  95

Val Asn Phe Lys Leu Leu Ser His Ser Leu Leu Val Thr Leu Ala Ser
            100                 105                 110

His Leu Pro Ser Asp Phe Thr Pro Ala Val His Ala Ser Leu Asp Lys
        115                 120                 125

Phe Leu Ala Asn Val Ser Thr Val Leu Thr Ser Lys Tyr Arg
    130                 135                 140
```

<210> SEQ ID NO 33
<211> LENGTH: 706
<212> TYPE: DNA
<213> ORGANISM: Bos taurus

<400> SEQUENCE: 33

```
atggtgctgt ctgccgccga caagggcaat gtcaaggccg cctggggcaa ggttggcggc      60
cacgctgcag agtatggcgc agaggccctg gagaggtgag caccgcactt gccccgaggg     120
gaccgggccg cacgccgggc gcgtccttgt cccgggccgc tcggcctaag cccggctttc     180
ccgcctcttc acccaggatg ttcctgagct tccccaccac caagacctac ttcccccact    240
tcgacctgag ccacggctcc gcgcaggtca agggccacgg cgcgaaggtg gccgccgcgc    300
tgaccaaagc ggtggaacac ctggacgacc tgcccggtgc cctgtctgaa ctgagtgacc    360
tgcacgctca caagctgcgt gtggacccgg tcaacttcaa ggtgagctcg cgggcagggc    420
cgggacagat ctgggctagc ggggcagaga atgcggcggc gccccaccc agccccgcc     480 cccctgacgt ccctctctc ggcagcttct gagccactcc ctgctggtga ccctggcctc    540
ccacctcccc agtgatttca ccccgcggt ccacgcctcc ctggacaagt tcttggccaa    600
cgtgagcacc gtgctgacct ccaaataccg ttaagctgga gcctcggcga ccctacccct    660
ggcctggagc cccttgcgc tctgcgcact ctcacctcct gatctt                     706
```

```
<210> SEQ ID NO 34
<211> LENGTH: 141
<212> TYPE: PRT
<213> ORGANISM: Sus scrofa

<400> SEQUENCE: 34

Val Leu Ser Ala Ala Asp Lys Ala Asn Val Lys Ala Ala Trp Gly Lys
 1               5                  10                  15

Val Gly Gly Gln Ala Gly Ala His Gly Ala Glu Ala Leu Glu Arg Met
                20                  25                  30

Phe Leu Gly Phe Pro Thr Thr Lys Thr Tyr Phe Pro His Phe Asn Leu
            35                  40                  45

Ser His Gly Ser Asp Gln Val Lys Ala His Gly Gln Lys Val Ala Asp
        50                  55                  60

Ala Leu Thr Lys Ala Val Gly His Leu Asp Asp Leu Pro Gly Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

His Pro Asp Asp Phe Asn Pro Ser Val His Ala Ser Leu Asp Lys Phe
        115                 120                 125

Leu Ala Asn Val Ser Thr Val Leu Thr Ser Lys Tyr Arg
        130                 135                 140

<210> SEQ ID NO 35
<211> LENGTH: 147
<212> TYPE: PRT
<213> ORGANISM: Sus scrofa

<400> SEQUENCE: 35

Met Val His Leu Ser Ala Glu Glu Lys Glu Ala Val Leu Gly Leu Trp
 1               5                  10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Asn Ala Asp Ala Val Met Gly Asn Pro Lys Val Lys Ala His
        50                  55                  60

Gly Lys Lys Val Leu Gln Ser Phe Ser Asp Gly Leu Lys His Leu Asp
65                  70                  75                  80

Asn Leu Lys Gly Thr Phe Ala Lys Leu Ser Glu Leu His Cys Asp Gln
                85                  90                  95

Leu His Val Asp Pro Glu Asn Phe Arg Leu Leu Gly Asn Val Ile Val
            100                 105                 110

Val Val Leu Ala Arg Arg Leu Gly His Asp Phe Asn Pro Asn Val Gln
        115                 120                 125

Ala Ala Phe Gln Lys Val Val Ala Gly Val Ala Asn Ala Leu Ala His
        130                 135                 140

Lys Tyr His
145
```